(12) United States Patent
Lesnicki et al.

(10) Patent No.: US 12,077,794 B2
(45) Date of Patent: *Sep. 3, 2024

(54) TEMPERATURE SHIFT FOR HIGH YIELD EXPRESSION OF POLYPEPTIDES IN YEAST AND OTHER TRANSFORMED CELLS

(71) Applicant: H. LUNDBECK A/S, Valby (DK)

(72) Inventors: Gary Lesnicki, Woodinville, WA (US); Mark Young, Boulder, CO (US)

(73) Assignee: H. LUNDBECK A/S, Valby (DK)

( * ) Notice: Subject to any disclaimer, the term of this patent is extended or adjusted under 35 U.S.C. 154(b) by 128 days.

This patent is subject to a terminal disclaimer.

(21) Appl. No.: 16/272,079

(22) Filed: Feb. 11, 2019

(65) Prior Publication Data
US 2019/0390239 A1   Dec. 26, 2019

Related U.S. Application Data

(62) Division of application No. 14/215,406, filed on Mar. 17, 2014, now Pat. No. 10,202,630.

(60) Provisional application No. 61/791,471, filed on Mar. 15, 2013.

(51) Int. Cl.
| | |
|---|---|
| *C12P 21/00* | (2006.01) |
| *C12N 1/16* | (2006.01) |
| *C12N 15/67* | (2006.01) |
| *C12N 15/90* | (2006.01) |

(52) U.S. Cl.
CPC .............. *C12P 21/00* (2013.01); *C12N 1/16* (2013.01); *C12N 15/67* (2013.01); *C12N 15/905* (2013.01); *C07K 2317/14* (2013.01); *C12N 2523/00* (2013.01)

(58) Field of Classification Search
CPC .......... C12N 15/09; C12N 15/81; C12N 1/16; C07K 16/00
See application file for complete search history.

(56) References Cited

U.S. PATENT DOCUMENTS

| | | | |
|---|---|---|---|
| 6,221,630 B1 | 4/2001 | Hopper | |
| 7,927,863 B2 | 4/2011 | Cregg et al. | |
| 10,138,294 B2* | 11/2018 | Lesnicki | C12P 21/02 |
| 10,202,630 B2* | 2/2019 | Lesnicki | C12N 1/16 |
| 2005/0053615 A1 | 3/2005 | Best et al. | |
| 2009/0162343 A1 | 6/2009 | Franano et al. | |
| 2009/0269832 A1 | 10/2009 | Jarrell et al. | |
| 2011/0189751 A1 | 8/2011 | Barnett | |
| 2013/0045888 A1 | 2/2013 | Mitchell et al. | |
| 2016/0031970 A1 | 2/2016 | Lesnicki et al. | |

FOREIGN PATENT DOCUMENTS

WO   2013/028635 A1   2/2013

OTHER PUBLICATIONS

Dragosits et al. 2009; The effect of temperature on the proteome of recombinant Pichia pastoris. Journal of Proteome Research. 8: 1380-1392.*
Baumann et al. 2007; Hypoxic fed-batch cultivation of Pichia pastoris increases specific and volumetric productivity of recombinant proteins. Biotechology and Bioengineering. 100(1): 177-183.*
Author Guidelines of Biotechology and Bioengineering. 2022; Author Guidelines, on the web at onlinelibrary.whiley.com/page/journal/10970290/homepage/forauthors.html. pp. 1-12.*
PLOS. 2022; How to write your methods. On line at plos.org/resource/how-to-write-your-methods/ pp. 1-7.*
Ghasemi et al. 2019; The principles of biomedical scientific writing: Materials and methods. Int. J. Endocrinol. Metab. 17(1): e88155, pp. 1-9.*
Potgieter et al. "Production of monoclonal antibodies by glycoengineered Pichia pastoris." Journal of biotechnology. Feb. 23, 2009;139(4):318-25.
Yu et al. "A novel robust heat-inducible promoter for heterologous gene expression in Tetrahymena thermophila." Protist. Mar. 1, 2012;163(2):284-95.
Reuveny S, et al. "Effect of temperature and oxygen on cell growth and recombinant protein production in insect cell cultures," Appl Microbiol Biotechnol. Feb. 1993;38(5):619-23.
Baumann, K. et al., "Hypoxic Fed-Batch Cultivation of Pichia pastoris Increases Specific and Volumetric Productivity of Recombinant Proteins", Biotechnology and Bioengineering, May 1, 2008, 100(1): 177-183.
Dragosits, M. et al., "The Effect of Temperature on the Proteome of Recombinant Pichia pastoris", Journal of Proteome Research, 2009, 8: 1380-1392.
Miller, M.J. et al., "A response of protein synthesis to temperature shift in the yeast *Saccharomyces cerevisiae*", Proc. Natl. Acad. Sci. USA, Oct. 1979, 76(10): 5222-5225.
Shi, X. et al., "Optimal Conditions for the expression of a single-chain antibody (scFv) gene in Pichia pastoris", Protein Expression and Purification, 2003, 28: 321-330.

* cited by examiner

*Primary Examiner* — Suzanne M Noakes
(74) *Attorney, Agent, or Firm* — Robin L. Teskin; Baker, Donelson, Bearman, Caldwell & Berkowitz PC

(57) ABSTRACT

Methods for producing heterologous proteins are disclosed. In particular, the present disclosure provides improved methods of producing desired proteins, including multi-subunit proteins such as antibodies, with a higher yield and improved purity. In exemplary embodiments, the transformed cells are a yeast, e.g., methylotrophic yeast such as *Pichia pastoris*.

18 Claims, 26 Drawing Sheets
Specification includes a Sequence Listing.

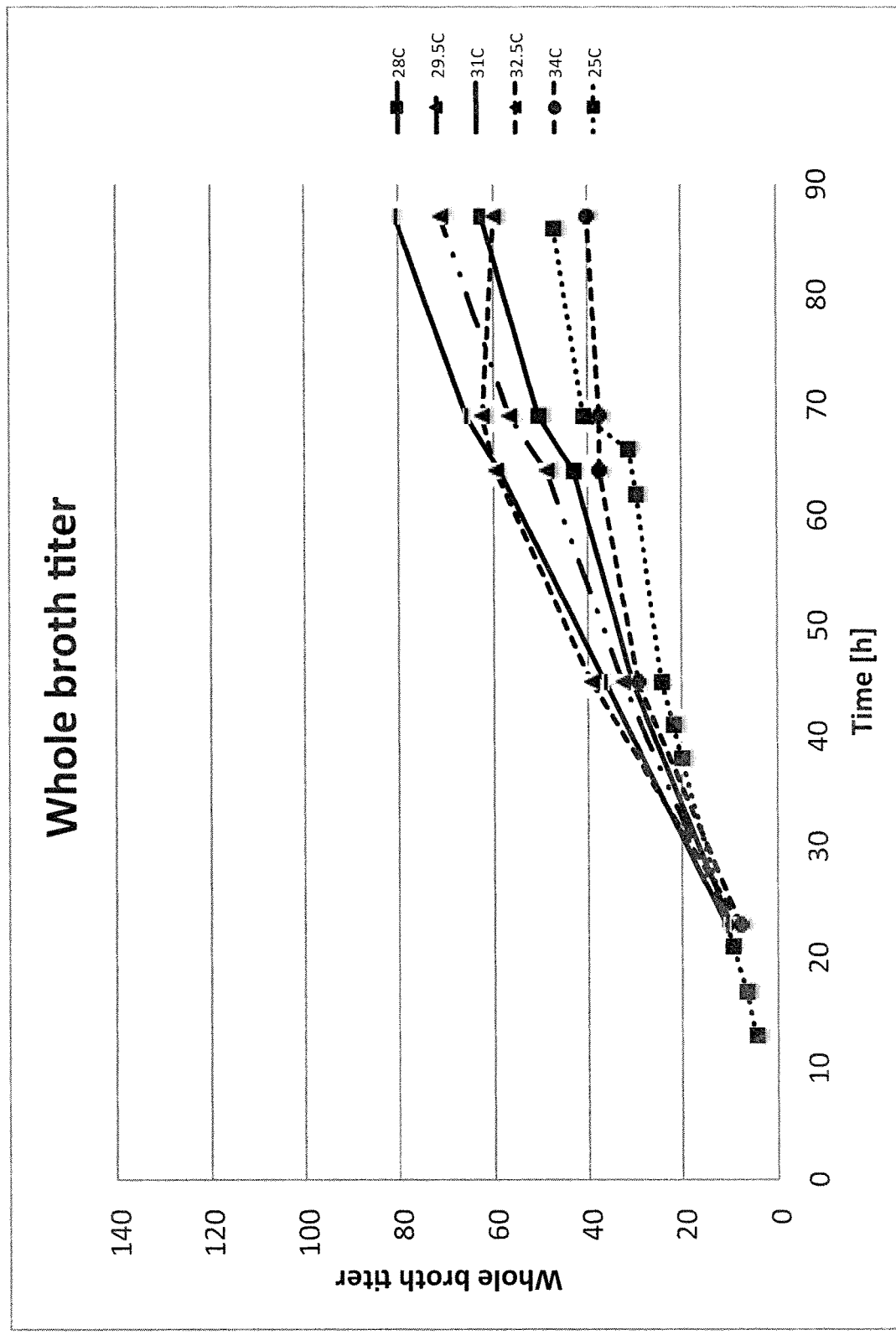
FIG. 1. Ab Titer Is Increased By Temperature Shift

Antibody Purity (Ab-A)

A. Non Reduced

| Temp C | Main peak IgG | Prepeak HHL | 75kD HL | Total |
|---|---|---|---|---|
| 25 | 86.3 | 7.1 | 1.7 | 95.1 |
| 28 | 89.0 | 6.8 | 1.7 | 97.5 |
| 29.5 | 88.7 | 6.8 | 1.8 | 97.3 |
| 31 | 88.0 | 7.5 | 1.6 | 97.1 |
| 32.5 | 70.4 | 7.3 | 16.3 | 94.0 |
| 34 | 73.8 | 7.1 | 15.0 | 95.9 |

FIG 2A

B. Reduced

| Temp C | HC | LC | RT 9.80 | RT 10.16 | RT 10.80 | Total HC+LC |
|---|---|---|---|---|---|---|
| 25 | 58.2 | 31.4 | 1.22 | 1.08 | 6.82 | 89.6 |
| 28 | 59.1 | 33.0 | 1.33 | 1.62 | 4.30 | 92.1 |
| 29.5 | 58.2 | 33.6 | 1.41 | 1.45 | 4.12 | 91.8 |
| 31 | 62.5 | 33.3 | 0.92 | 0.72 | 1.95 | 95.8 |
| 32.5 | 64.0 | 31.6 | 0.50 | 0.23 | 2.15 | 95.6 |
| 34 | 64.3 | 31.8 | 0.42 | 0.11 | 2.07 | 96.1 |

FIG 2B

Fig. 3A. Ab-A temperature shift to 25° C
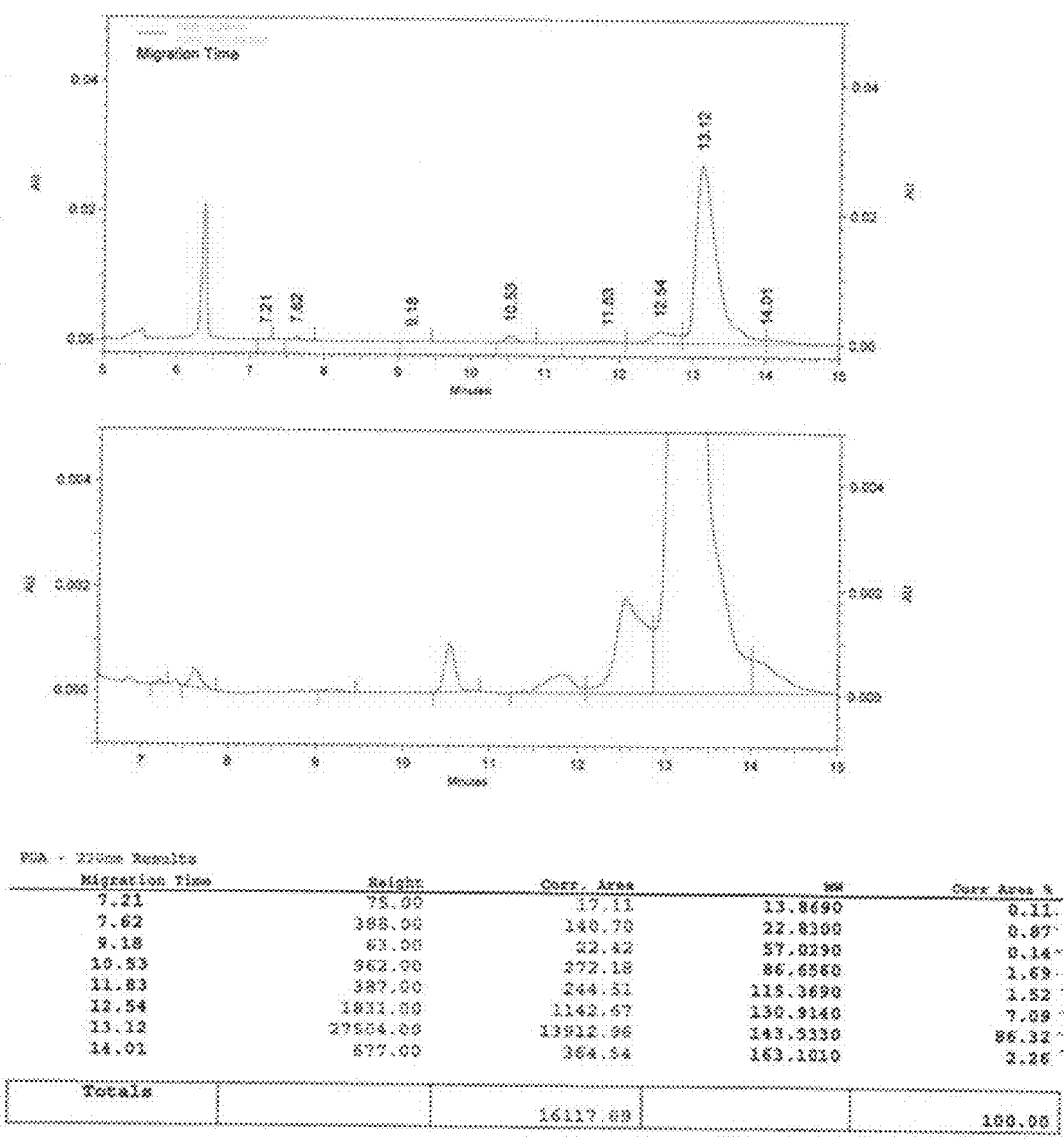

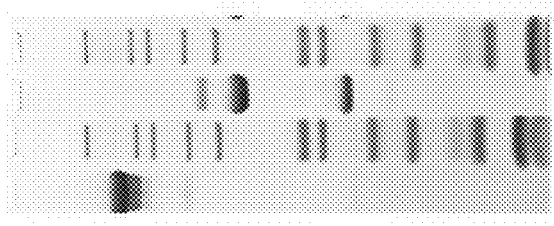
Fig. 3B. Ab-A temperature shift to 25° C

Fig. 3C. Ab-A temperature shift to 25° C
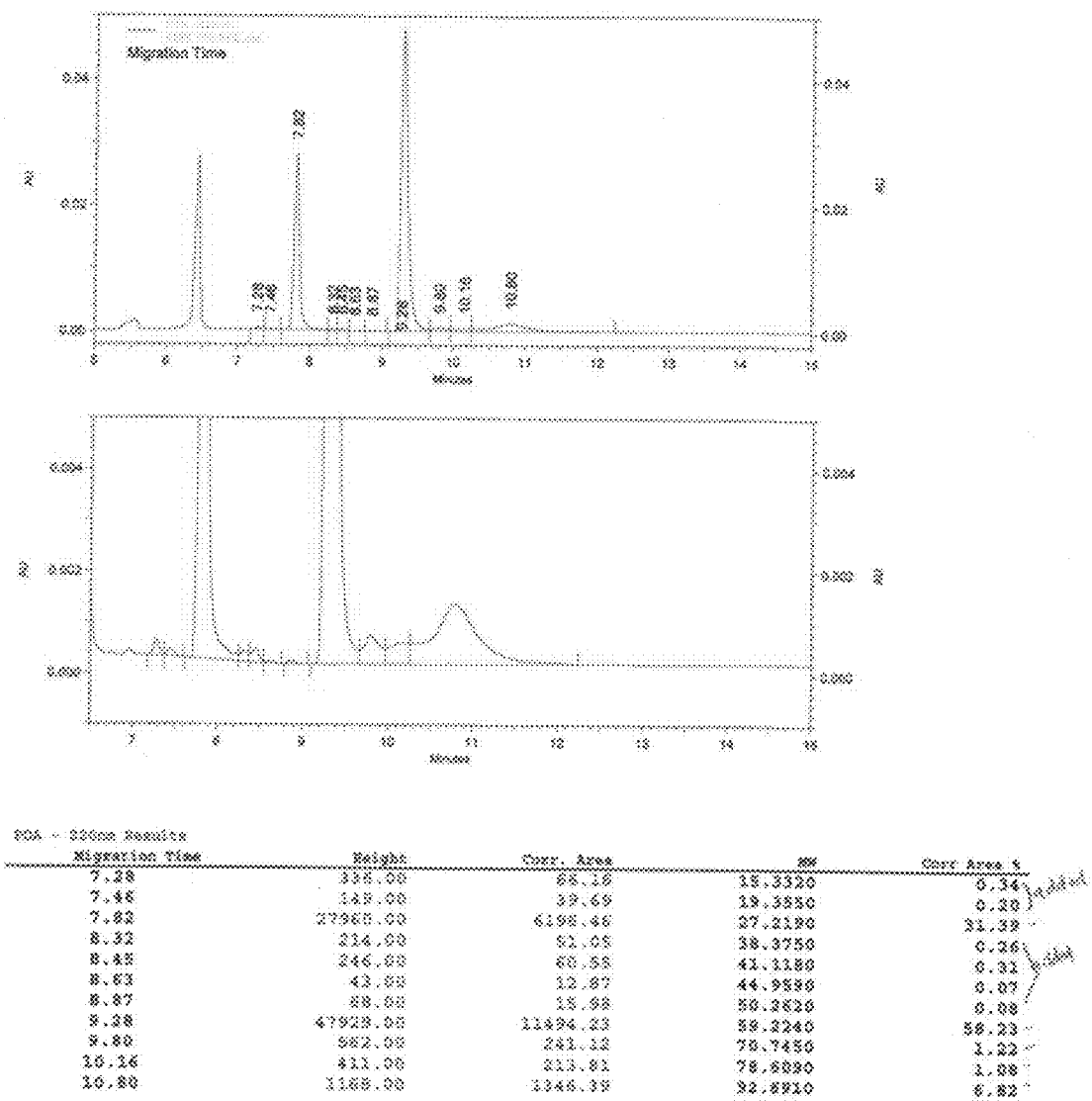

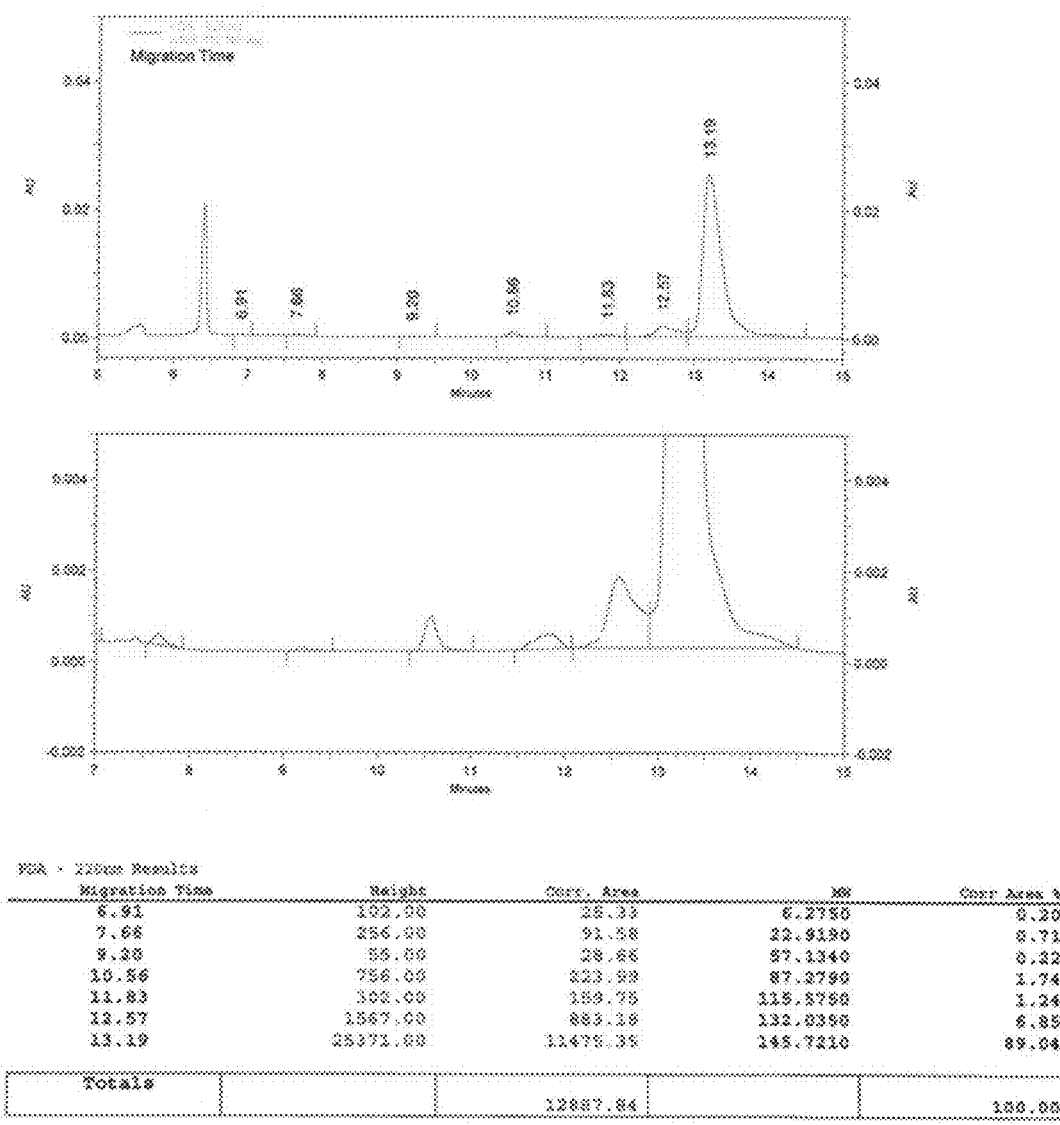
Fig. 4A. Ab-A maintained at 28° C (no shift)

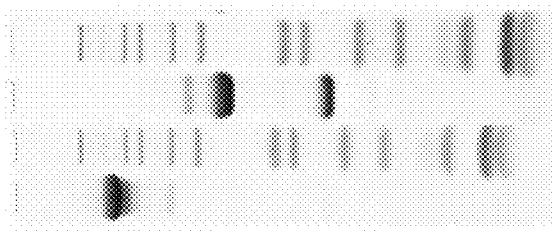
Fig. 4B. Ab-A maintained at 28° C (no shift)

Fig. 4C. Ab-A maintained at 28° C (no shift)
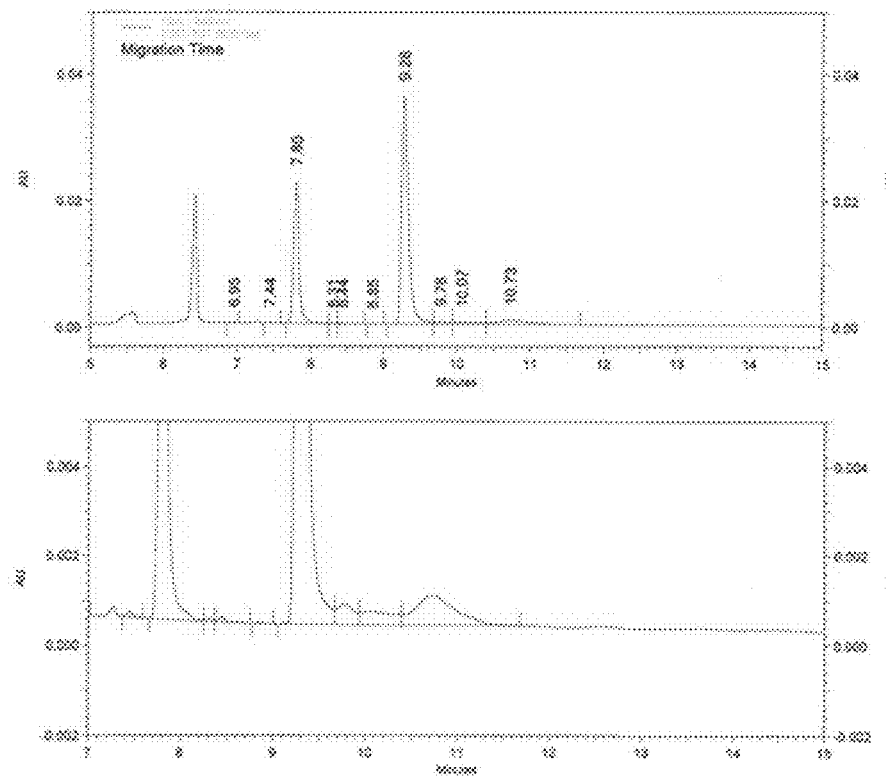

FIG. 5A. Ab-A temperature shift to 29.5° C
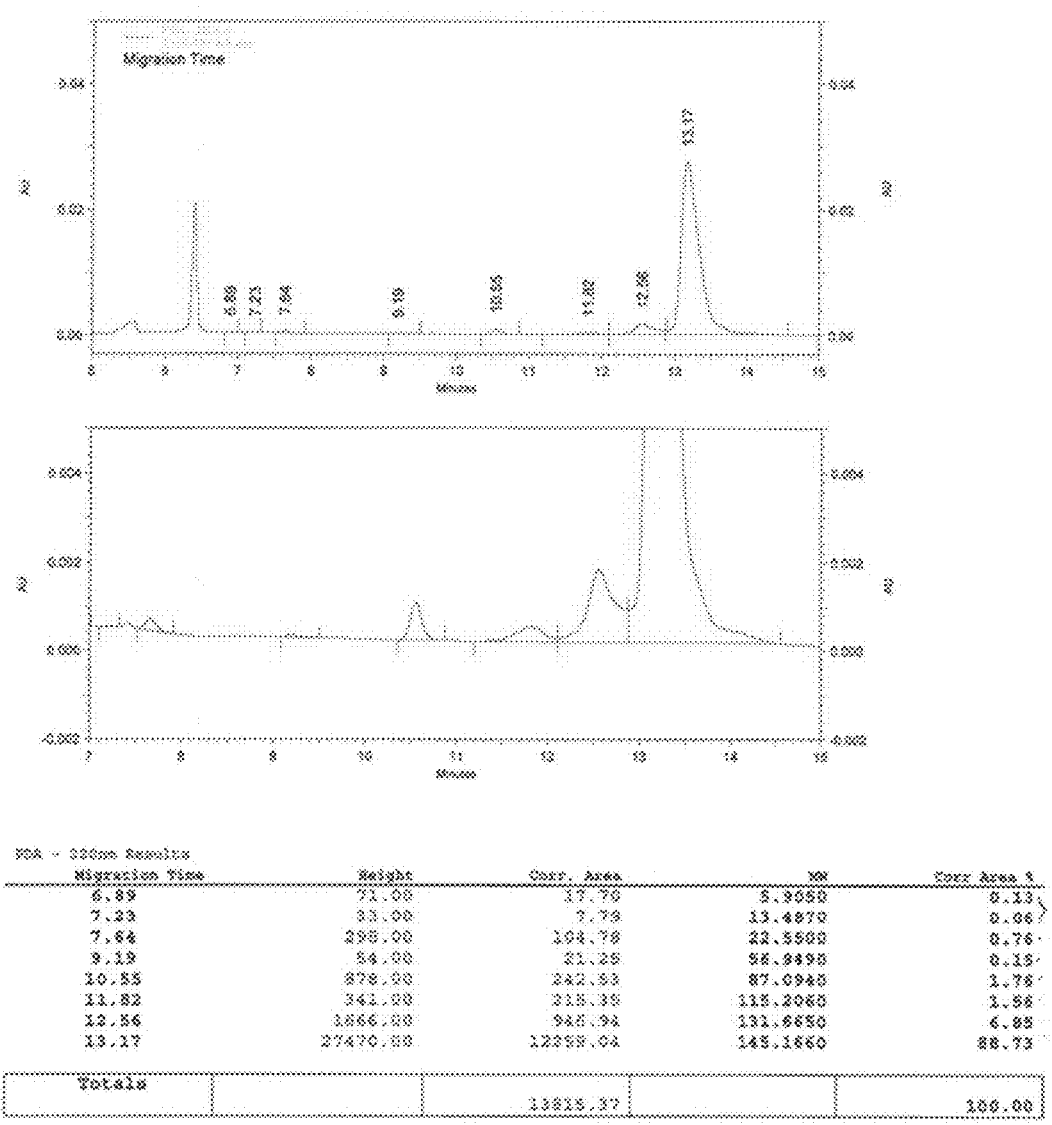

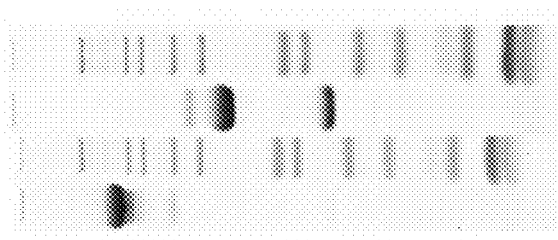
FIG. 5B. Ab-A temperature shift to 29.5° C

FIG. 5C. Ab-A temperature shift to 29.5° C
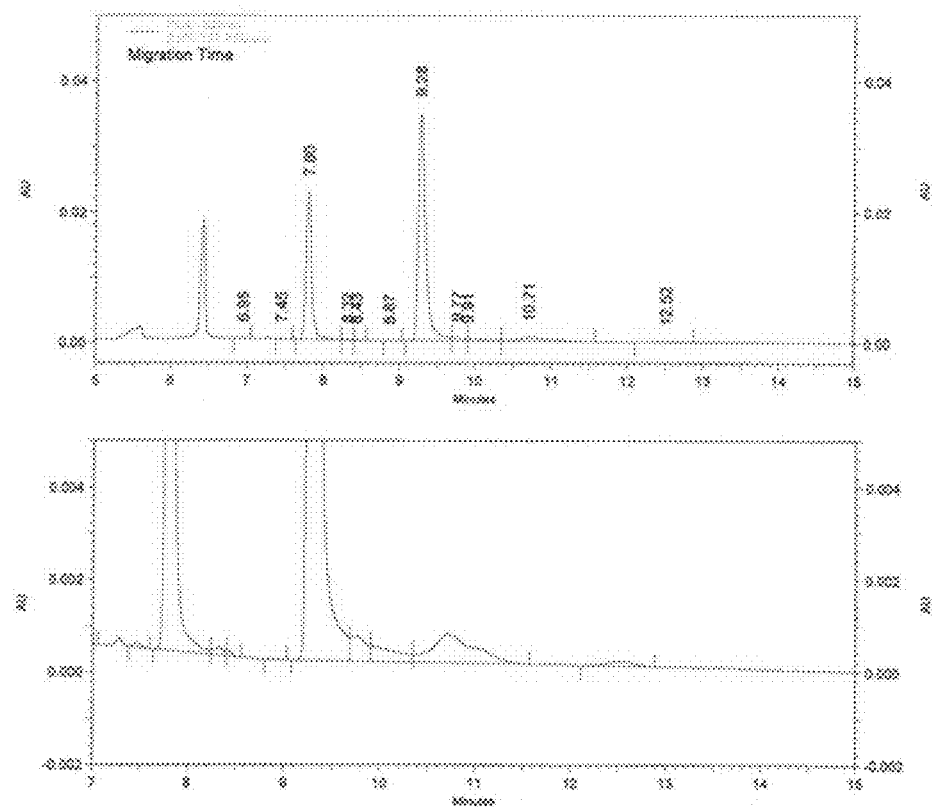

FIG. 6A. Ab-A temperature shift to 31° C
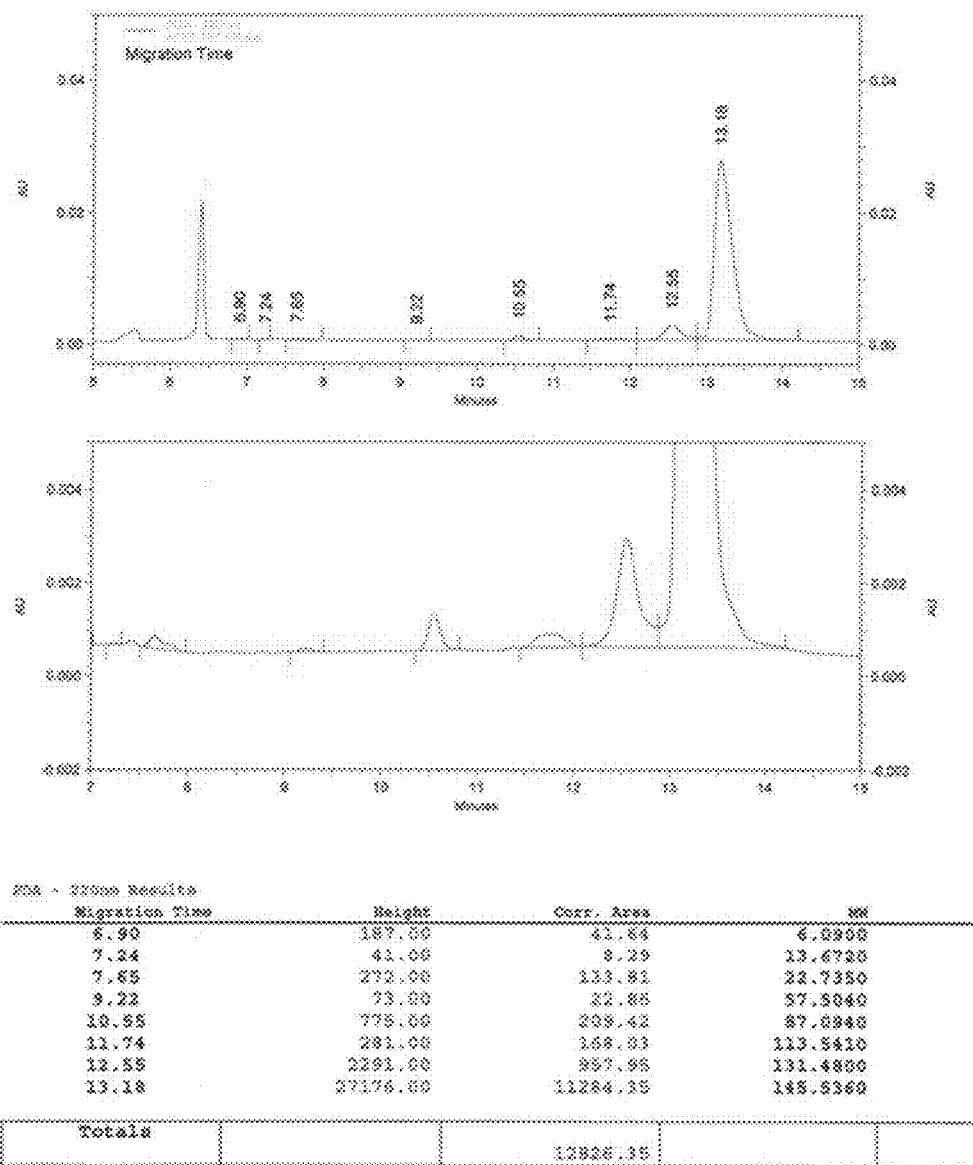

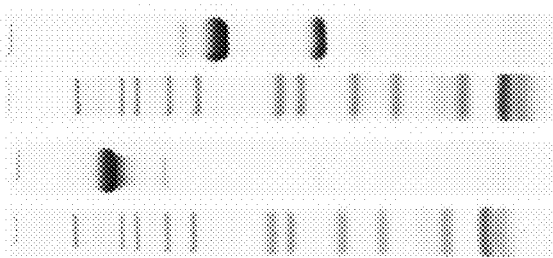
FIG. 6B. Ab-A temperature shift to 31° C

FIG. 6C. Ab-A temperature shift to 31° C
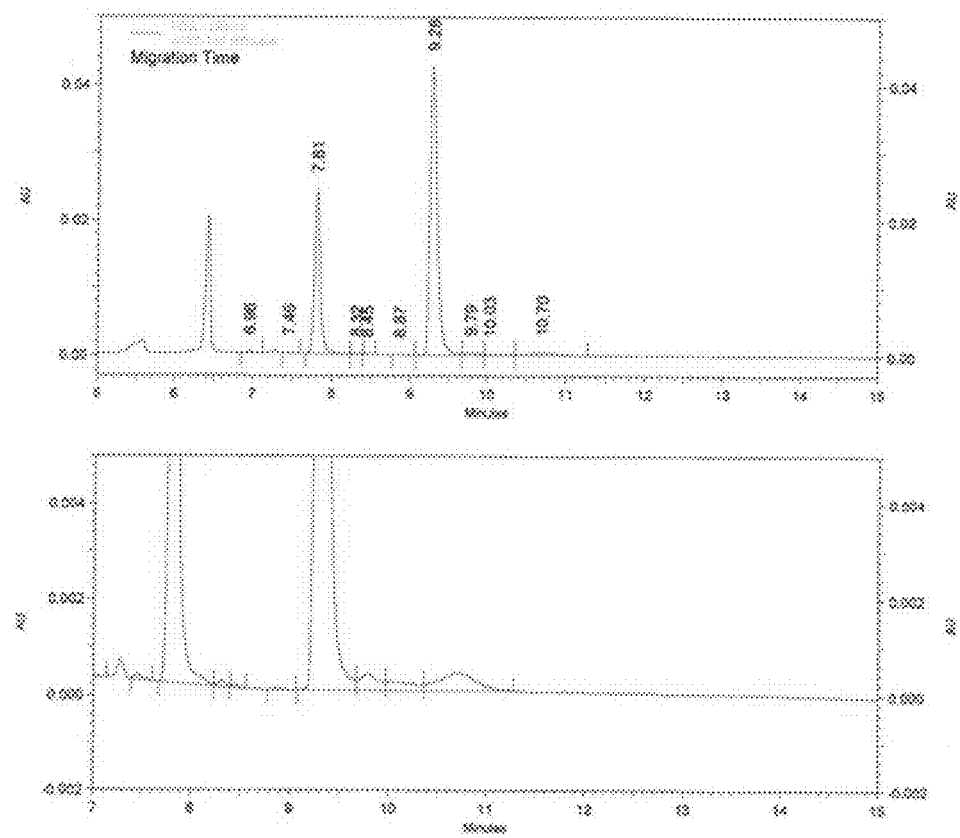

FIG. 7A. Ab-A temperature shift to 32.5° C
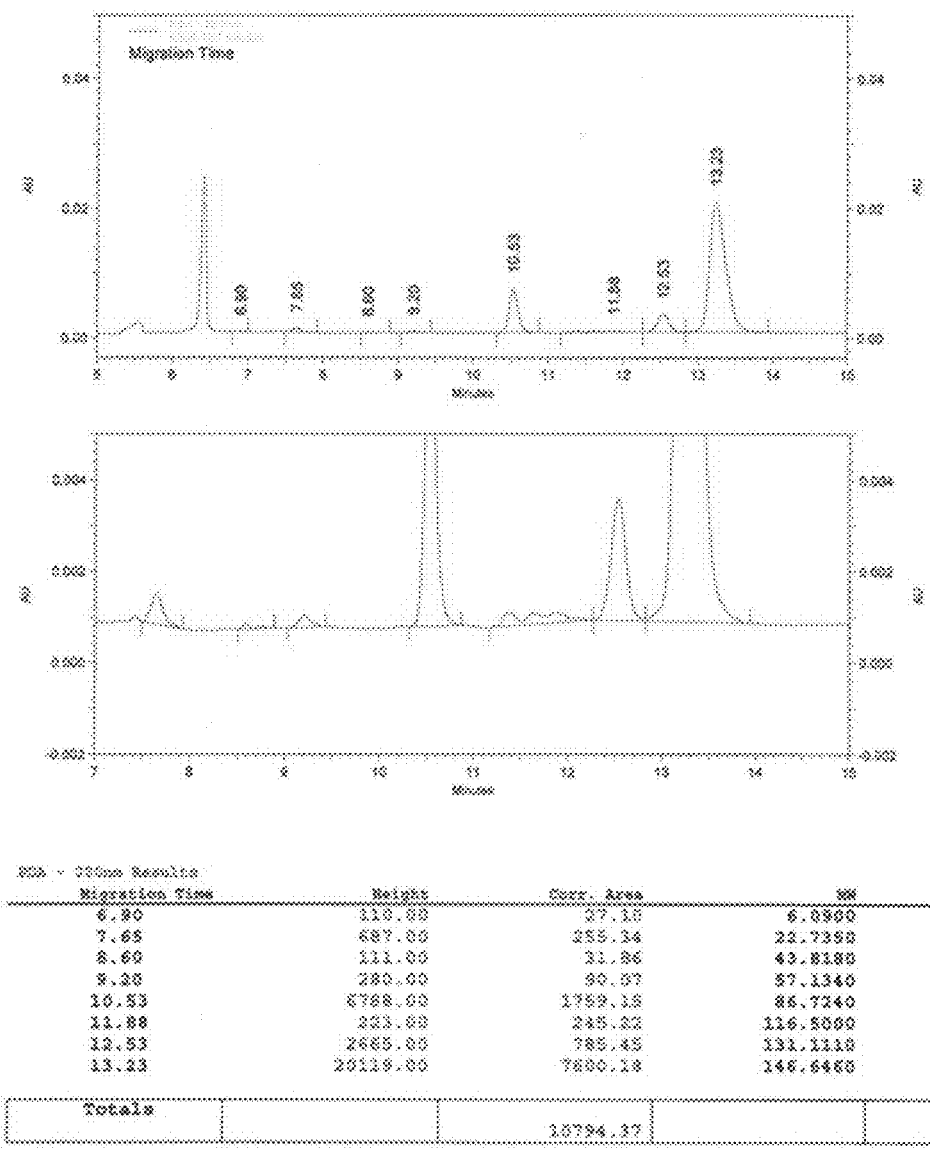

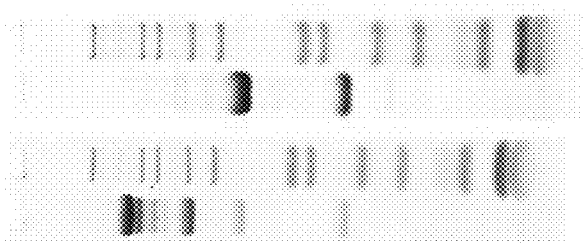
FIG. 7B. Ab-A temperature shift to 32.5° C

FIG. 7C. Ab-A temperature shift to 32.5° C
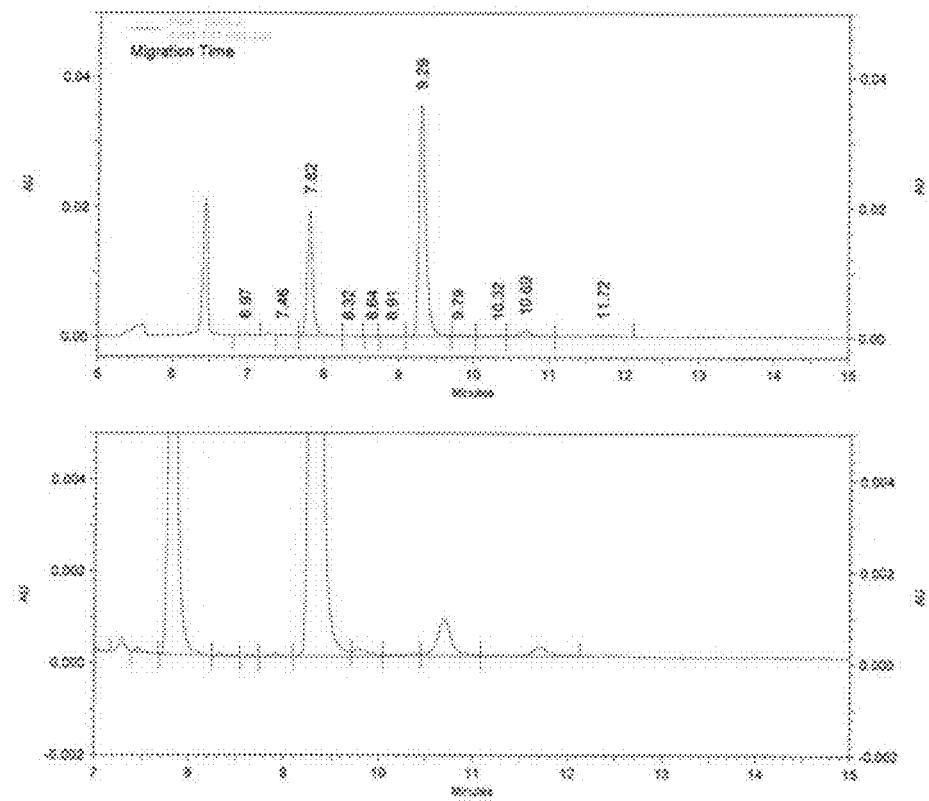

FIG. 8A. Ab-A temperature shift to 34° C
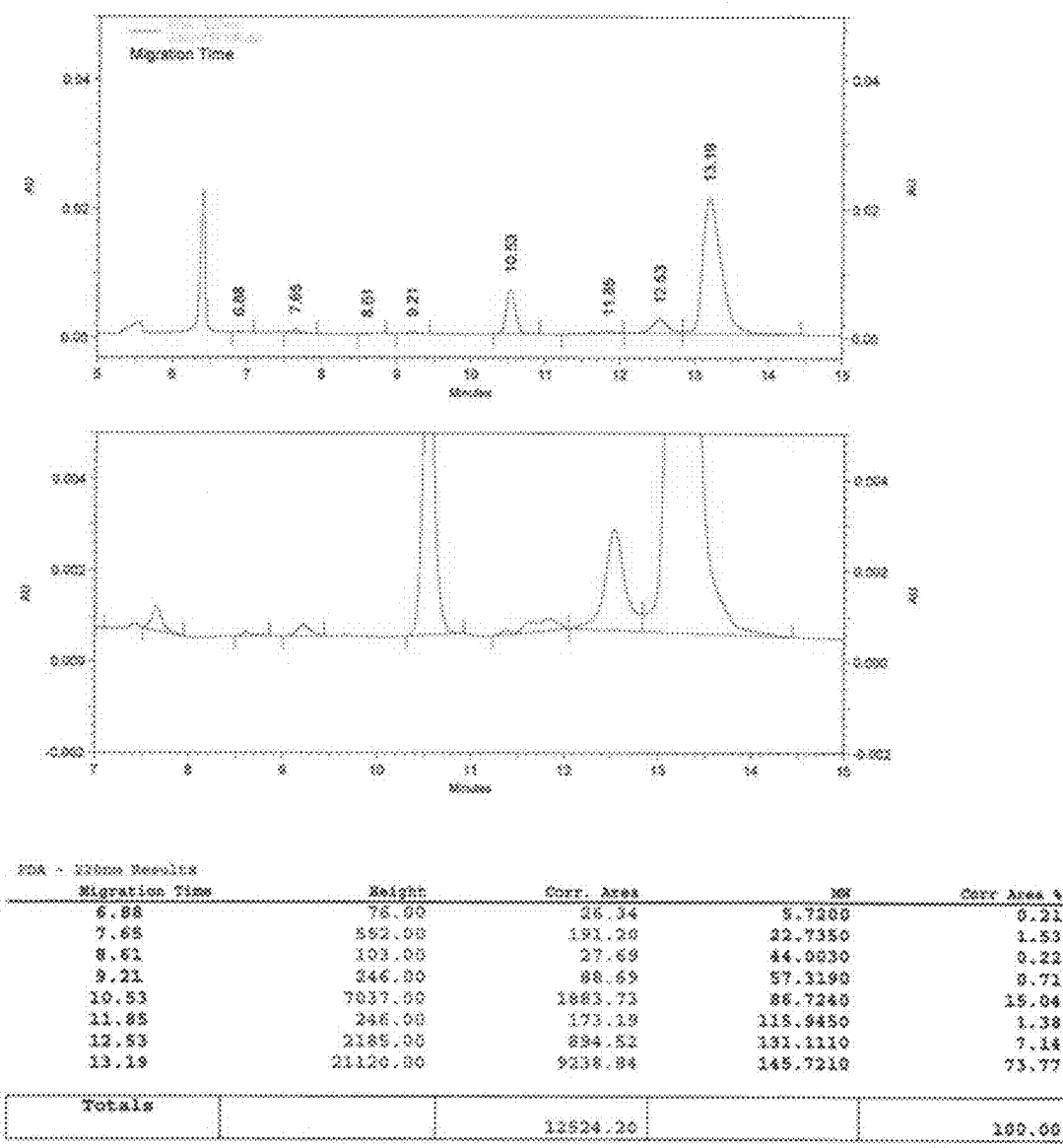

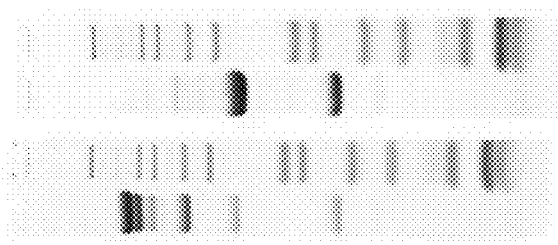
FIG. 8B. Ab-A temperature shift to 34° C

FIG. 8C. Ab-A temperature shift to 34° C
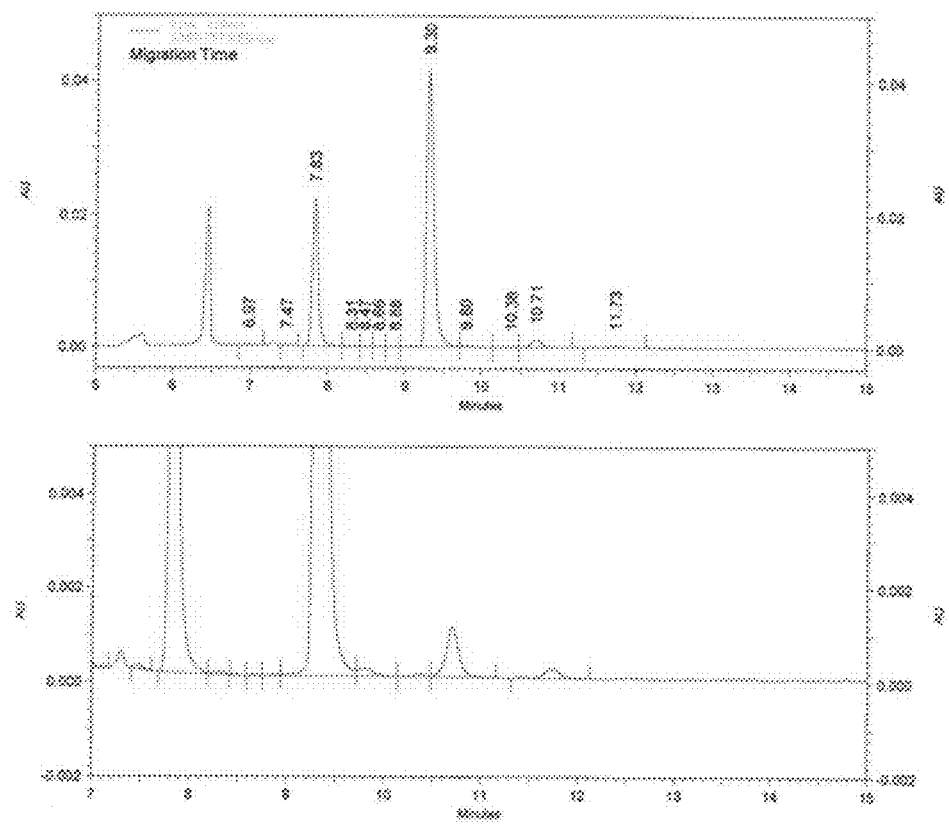

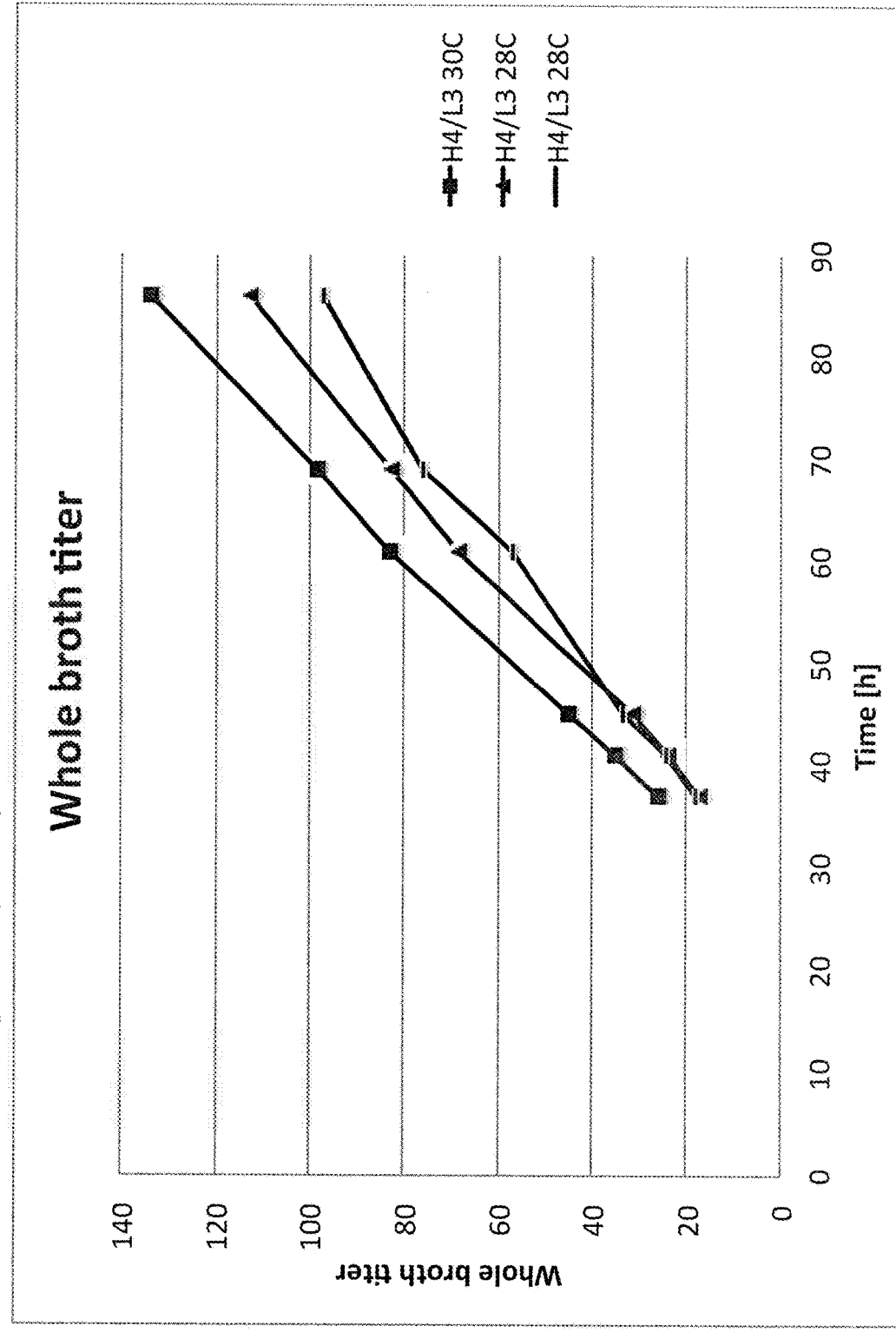

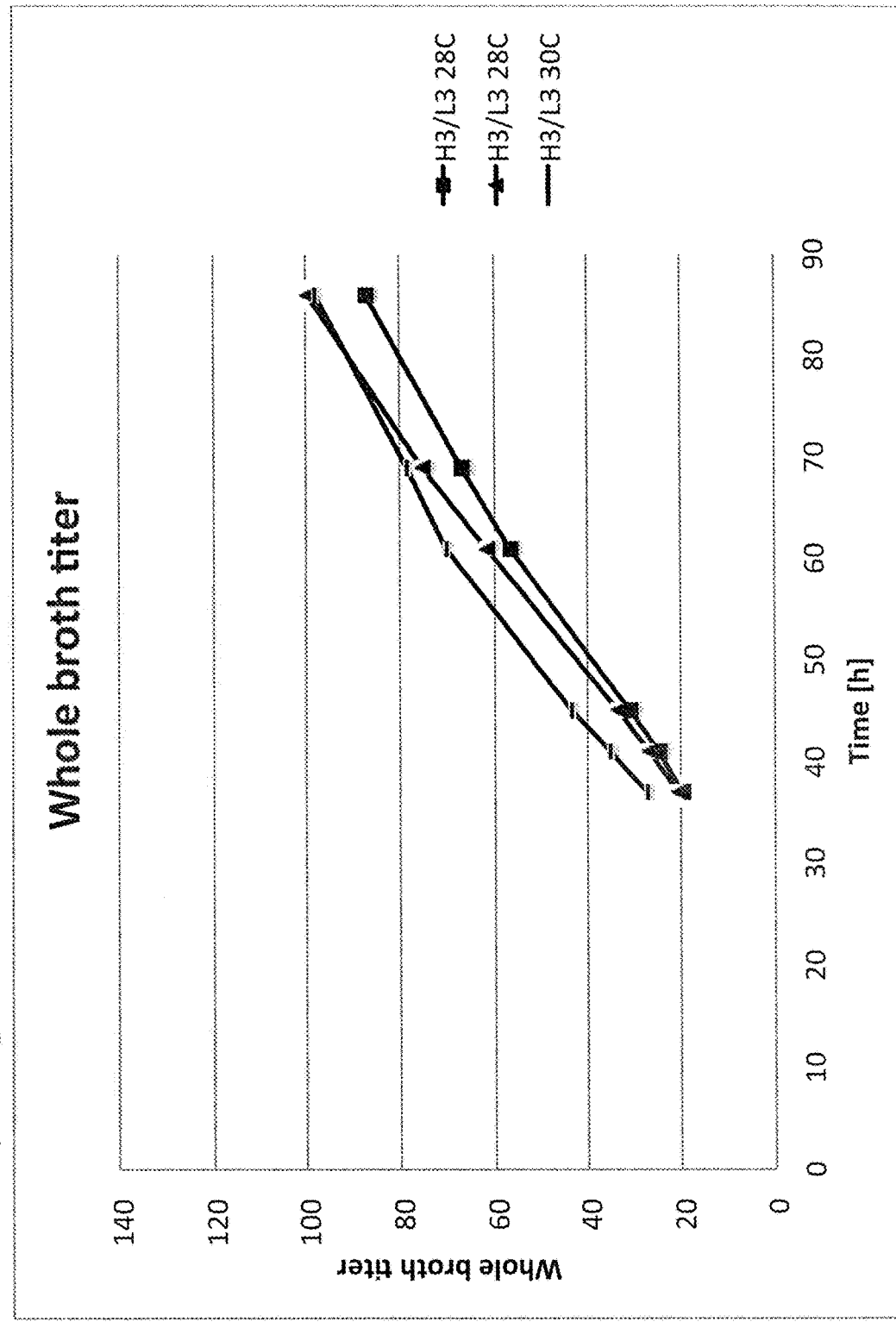
FIG 9B  Ab Titer Is Increased By Temperature Shift
B. Lower-expressing strain (H3/L3)

FIG. 10. Antibody Purity (Ab-B)

Non Reduced

| Temp C | Main peak IgG | Prepeak HHL | 75kD HL | Total |
|---|---|---|---|---|
| 28 | 89.34 | 3.27 | 1.52 | 94.13 |
| 28 | 76.25 | 7.35 | 8.00 | 91.60 |
| 30 | 91.63 | 2.94 | 1.44 | 96.01 |
| 30 | 83.44 | 4.75 | 6.15 | 94.34 |
| 28 | 87.72 | 3.60 | 2.15 | 93.47 |
| 28 | 61.05 | 4.92 | 23.14 | 89.11 |

Reduced

| Temp C | HC | LC | RT 10.15 | RT 10.60 | RT 11.08 | Total HC/LC |
|---|---|---|---|---|---|---|
| 28 | 67.67 | 29.58 | 0.90 | 0.00 | 0.55 | 97.25 |
| 28 | 63.75 | 30.62 | 0.69 | 0.00 | 0.53 | 94.37 |
| 30 | 67.91 | 29.83 | 0.82 | 0.00 | 0.42 | 97.74 |
| 30 | 67.20 | 29.55 | 1.04 | 0.00 | 0.57 | 96.75 |
| 28 | 67.66 | 29.50 | 0.85 | 0.00 | 0.71 | 97.16 |
| 28 | 65.42 | 29.64 | 0.89 | 0.00 | 0.89 | 95.06 |

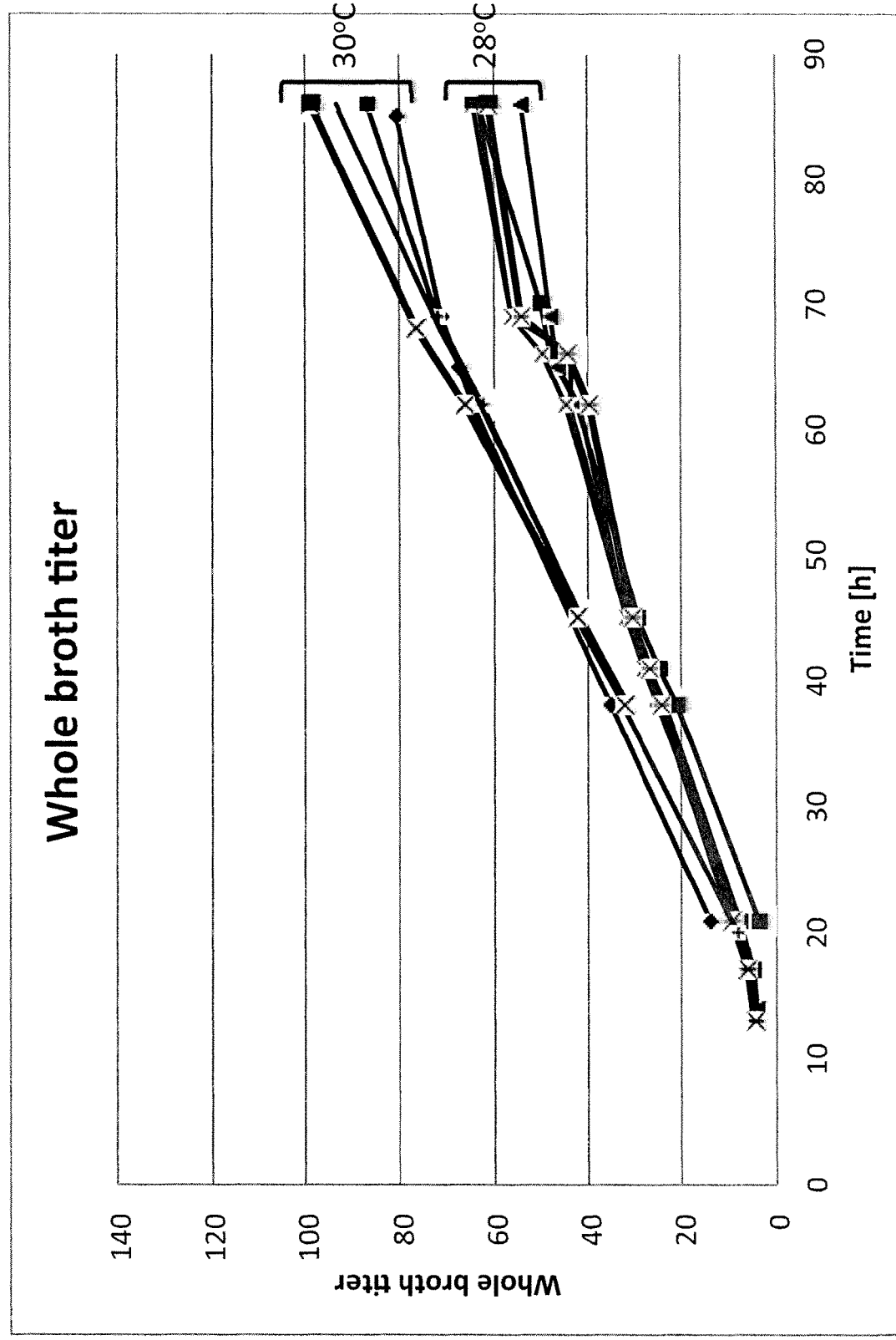
FIG. 11. Ab Titer Is Increased By Temperature Shift

FIG. 12. Ab-A Purity

Non Reduced

| Temp C | Main peak IgG | Prepeak HHL | 75kD HL | Total |
|---|---|---|---|---|
| 28 | 85.64 | 8.23 | 1.54 | 95.41 |
| 28 | 84.97 | 7.9 | 1.55 | 94.42 |
| 28 | 85.87 | 7.63 | 1.63 | 95.13 |
| 28 | 85.75 | 7.96 | 1.5 | 95.21 |
| 28 | 85.96 | 7.52 | 1.84 | 95.32 |
| 30 | 87.88 | 6.71 | 1.69 | 96.28 |
| 30 | 86.64 | 7.07 | 1.79 | 95.5 |
| 30 | 89.54 | 5.12 | 2.55 | 97.21 |
| 30 | 86.56 | 6.02 | 4.1 | 96.68 |

Reduced

| Temp C | HC | LC | RT 9.80 | RT 10.16 | RT 10.80 | Total HC/LC |
|---|---|---|---|---|---|---|
| 28 | 60.88 | 32.23 | 0.96 | 1.02 | 2.69 | 93.11 |
| 28 | 60.31 | 32.21 | 1.06 | 1.26 | 3.78 | 92.52 |
| 28 | 59.24 | 31.53 | 1.21 | 1.57 | 5.18 | 90.77 |
| 28 | 59.47 | 32.05 | 1.11 | 1.37 | 4.79 | 91.52 |
| 28 | 60.05 | 31.69 | 1.16 | 1.27 | 4.5 | 91.74 |
| 30 | 63.8 | 31.75 | 0.84 | 0.76 | 1.97 | 95.55 |
| 30 | 64.47 | 32.04 | 0.8 | 0.61 | 0.89 | 96.51 |
| 30 | 66.52 | 31.26 | 0.79 | 0 | 0.97 | 97.78 |
| 30 | 66.33 | 31.09 | 0.83 | 0 | 1.24 | 97.42 |

TEMPERATURE SHIFT FOR HIGH YIELD EXPRESSION OF POLYPEPTIDES IN YEAST AND OTHER TRANSFORMED CELLS

PRIORITY APPLICATION INFORMATION

This application is a divisional of U.S. application Ser. No. 14/215,406, filed Mar. 17, 2014, which claims priority to U.S. Provisional Application No. 61/791,471, filed Mar. 15, 2013, each of which is hereby incorporated by reference in its entirety herein.

The instant application contains a Sequence Listing which has been submitted in ASCII format via EFS-Web and is hereby incorporated by reference in its entirety. Said ASCII copy, created on Feb. 11, 2019, is named 4325703405.txt and is 14,236 bytes in size.

FIELD

The present disclosure generally relates to methods for producing desired proteins in yeast and other cells. Included in the disclosure are methods that can be used to express single- and multi-subunit proteins, including antibodies. In exemplary embodiments, the cells are a yeast, such as *Pichia pastoris*. Embodiments of the subject methods can produce antibodies or other desired proteins with increased yield as compared to conventional methods.

BACKGROUND

Numerous recombinantly produced proteins have received regulatory approval for human therapeutic use. A growing number of these therapeutic proteins are produced in microbial expression systems. Indeed, according to a recent review, microbial expression systems are used for production of nearly half of the 151 protein-based recombinant pharmaceuticals licensed up to January 2009 by the U.S. Food and Drug Administration or European Medicines Agency (Ferrer-Miralles et al., Microbial Cell Factories 2009, 8:17).

Among these recombinantly produced proteins are antibodies, which conventionally are tetrameric proteins composed of two identical light chains and two identical heavy chains. Hundreds of therapeutic monoclonal antibodies (mAbs) are currently either on the market or under development. The production of functional antibodies generally involves the synthesis of the two polypeptide chains as well as a number of post-translational events, including proteolytic processing of the N-terminal secretion signal sequence; proper folding and assembly of the polypeptides into tetramers; formation of disulfide bonds; and typically includes a specific N-linked glycosylation.

Fungal hosts such as the methylotrophic yeast *Pichia pastoris* have distinct advantages for therapeutic protein expression, including that they do not secrete high amounts of endogenous proteins, have strong inducible promoters available for producing heterologous proteins, can be grown in defined chemical media and without the use of animal sera, and can produce high titers of recombinant proteins (Cregg et al., FEMS Microbiol. Rev. 24: 45-66 (2000)). Prior work, including work conducted by the present inventors, has helped established *P. pastoris* as a cost-effective platform for producing functional antibodies that are suitable for research, diagnostic, and therapeutic use. See co-owned U.S. Pat. Nos. 7,927,863 and 7,935,340, each of which is incorporated by reference herein in its entirety. Methods are also known in the literature for design of *P. pastoris* fermentations for expression of recombinant proteins, with optimization having been described with respect to parameters including cell density, broth volume, pH, substrate feed rate, and the length of each phase of the reaction. See Zhang et al., "Rational Design and Optimization of Fed-Batch and Continuous Fermentations" in Cregg, J. M., Ed., 2007, *Pichia* Protocols (2nd edition), Methods in Molecular Biology, vol. 389, Humana Press, Totowa, N.J., pgs. 43-63, which is hereby incorporated by reference in its entirety.

Additionally, prior work by the present applicants and others has described increasing production of proteins in yeast through methods including addition of a bolus of ethanol to the culture at or near the beginning of the production phase, and with respect to multi-subunit proteins such as antibodies, varying the number of gene copies and the copy number ratio between subunit genes. See US20130045888, entitled, Multi-Copy Strategy For High-Titer And High-Purity Production Of Multi-Subunit Proteins Such As Antibodies In Transformed Microbes Such As *Pichia Pastoris*; and US20120277408, entitled, High-Purity Production Of Multi-Subunit Proteins Such As Antibodies In Transformed Microbes Such As *Pichia Pastoris*.

Though the aforementioned Zhang et al. article makes some effort to describe a systematic approach to optimizing the aforementioned parameters and give a theoretical approach to understanding the interplay between some of these parameters, expression optimization remains a largely empirical process. Because of this interplay, it is generally insufficient to optimize each individual parameter while keeping all others constant. For example, optimal media composition may vary with culture density, strain background, feed rate, agitation, oxygenation, etc. Because of this complex interplay, the number of combinations of parameters that can be tested is potentially infinite, and even if an expression system has been extensively optimized there always remain a large number of untested conditions which could benefit yield and/or purity.

SUMMARY

As further described below, Applicants have identified methods of greatly increasing the yield of recombinant proteins produced in eukaryotic cells such as yeast. Even for expression systems which had already been highly optimized, the subject method increased the yield of recombinant protein by up to about 30%.

In one aspect, the disclosure provides a method of producing a desired protein, comprising: (a) culturing eukaryotic cells comprising one or more genes that provide for the expression of said desired protein at a first temperature; and (b) culturing said eukaryotic cells at a second temperature and allowing said eukaryotic cells to produce said desired protein; wherein said second temperature is different than said first temperature.

Said first temperature may be between about 20 degrees C. and about 32 degrees C.

Said first temperature may be between about 24 degrees C. and about 31.5 degrees C.

Said first temperature may be between about 27 degrees C. and about 31 degrees C.

Said first temperature may be between about 27.5 degrees C. and about 30 degrees C.

Said first temperature may be between about 20 degrees C. and about 29.5 degrees C.

Said first temperature may be between about 24 degrees C. and about 29 degrees C.

Said first temperature may be between about 27 degrees C. and about 28.5 degrees C.

Said first temperature may be between about 27.5 degrees C. and about 28.5 degrees C.

Said second temperature may be between about 1 degree C. and about 6 degrees C. higher than said first temperature.

Said second temperature may be between about 1 degree C. and about 3 degrees C. higher than said first temperature.

Said second temperature may be between about 2 degrees C. and about 4 degrees C. higher than said first temperature.

Said second temperature may be between about 2 degrees C. and about 3 degrees C. higher than said first temperature.

Said second temperature may be between about 30 degrees C. and about 34 degrees C.

Said second temperature may be between about 30 degrees C. and about 32 degrees C.

Said second temperature may be between about 30 degrees C. and about 31.5 degrees C.

Said second temperature may be about 30 degrees C. or about 31 degrees C.

Said second temperature may be higher than said first temperature.

Said desired protein comprises a multi-subunit complex.

Said multi-subunit complex may comprise an antibody.

Said antibody may be human or humanized.

Said antibody may be specific for IL-6, TNFalpha, CGRP, PCSK9, HGF, or NGF.

Said method may increase the yield of said desired protein.

Said method may decrease the relative abundance of one or more product-associated variants relative to the same method effected without a difference between said first temperature and said second temperature.

Said method may decrease the relative abundance of product-associated variants having a higher or lower apparent molecular weight than said desired multi-subunit complex as detected by size exclusion chromatography or gel electrophoresis relative to the same method effected without a difference between said first temperature and said second temperature.

Said method may decrease the relative abundance of complexes having aberrant disulfide bonds relative to the same method effected without a difference between said first temperature and said second temperature.

Said method may decrease the relative abundance of complexes having reduced cysteines relative to the same method effected without a difference between said first temperature and said second temperature.

Said method may decrease the relative abundance of complexes having aberrant glycosylation relative to the same method effected without a difference between said first temperature and said second temperature.

Said method may decrease the relative abundance of one or more product-associated variants relative to the same method effected without a difference between said first temperature and said second temperature.

Said eukaryotic cells may comprise yeast cells.

Said yeast cells may comprise methylotrophic yeast.

Said methylotrophic yeast may be of the genus *Pichia*.

Said methylotrophic yeast of the genus *Pichia* may be *Pichia pastoris*.

Said methylotrophic yeast of the genus *Pichia* may be selected from the group consisting of: *Pichia angusta*, *Pichia guillermordii*, *Pichia methanolica*, and *Pichia inositovera*.

The genes that provide for expression of said desired protein may be integrated into one or more genomic loci.

At least one of said genomic loci may be selected from the group consisting of the pGAP locus, 3' AOX TT locus; PpURA5; OCH1; AOX1; HIS4; GAP; pGAP; 3' AOX TT; ARG; and the HIS4 TT locus.

At least one of the genes encoding said subunits of said desired protein may be expressed under control of an inducible or constitutive promoter.

Said inducible promoter may be selected from the group consisting of the AOX1, CUP1, tetracycline inducible, thiamine inducible, and FLD1 promoters.

Step (a) may comprise culturing said eukaryotic cells in a culture medium comprising glycerol as a carbon source until said glycerol is exhausted.

Said desired protein may be expressed under control of a promoter selected from the group consisting of: the CUP1, AOX1, ICL1, glyceraldehyde-3-phosphate dehydrogenase (GAP), FLD, ADH1, alcohol dehydrogenase II, GAL4, PHO3, PHO5, and Pyk promoters, tetracycline inducible promoters, thiamine inducible promoters, chimeric promoters derived therefrom, yeast promoters, mammalian promoters, insect promoters, plant promoters, reptile promoters, amphibian promoters, viral promoters, and avian promoters.

Said eukaryotic cell may be a diploid, tetraploid cell, or polyploid.

The method may further comprise purifying said desired protein from said eukaryotic cells or from the culture medium.

Said desired protein may be purified from an intracellular component, cytoplasm, nucleoplasm, or a membrane of said eukaryotic cells.

Said eukaryotic cells may secrete said desired protein into the culture medium.

Step (a) may comprise a batch phase.

Said batch phase may comprise culturing the eukaryotic cell in a medium comprising a carbon source.

The end of said batch phase may be determined by exhaustion of the carbon source in the culture medium.

Step (b) may comprise a fed batch phase.

The respiratory quotient (RQ) may be maintained at a specified value or in a specified range during step (b).

Said specified RQ value may be about 1.12.

Said specified RQ range may be about 1.0 to 1.24, or about 1.06 to 1.18, or about 1.09 to 1.15.

Said RQ value may or said RQ range may be maintained by modulating one or more of the feed rate, feed composition, supplied air flow rate, agitation rate, and/or oxygen concentration of supplied air.

The method may comprise a batch phase and a fed batch phase.

The batch phase may comprise culturing the eukaryotic cells with a carbon source until said carbon source is depleted. Said carbon source may comprise one or more of: glycerol, glucose, ethanol, citrate, sorbitol, xylose, trehalose, arabinose, galactose, fructose, melibiose, lactose, maltose, rhamnose, ribose, mannose, mannitol, and raffinose, and preferably comprises glycerol.

The fed batch phase may be initiated after the batch phase.

The temperature shift may be effected at or near the end of the batch phase, at or near the beginning of the fed batch phase, between the batch phase and the fed batch phase.

For example the temperature shift may be effected after depletion of the carbon source, or prior to commencing feed addition, or subsequent to commencing feed addition.

Preferably the temperature shift is effected less than 5 hours after commencing feed addition, e.g., less than 4 hours, less than 3 hours, less than 2 hours, less than 1 hour, less than 30 minutes, less than 20 minutes, or less than 5 minutes after commencing feed addition. However, the temperature shift may be effected at an earlier or later time.

The method may include the addition of an ethanol bolus to the culture. The ethanol bolus may be added concurrently with the exhaustion of the carbon source added to the initial culture, which may be detected by a rapid increase in the dissolved oxygen concentration (dissolved oxygen spike) or by other means.

The ethanol bolus may result in a concentration of ethanol in the culture of between about 0.01% and about 4%, between about 0.02% and about 3.75%, between about 0.04% and about 3.5%, between about 0.08% and about 3.25%, between about 0.1% and about 3%, between about 0.2% and about 2.75%, between about 0.3% and about 2.5%, between about 0.4% and about 2.25%, between about 0.5% and about 1.5%, between about 0.5% and about 2%, between about 0.6% and about 1.75%, between about 0.7% and about 1.5%, or between about 0.8% and about 1.25%.

The ethanol bolus may result in a concentration of ethanol in the culture of that may be at least about 0.01%, 0.02%, 0.03%, 0.04%, 0.05%, 0.06%, 0.07%, 0.08%, 0.09%, 0.10%, 0.2%, 0.3%, 0.4%, 0.5%, 0.6%, 0.7%, 0.8% or 0.9% (w/v).

The ethanol bolus may result in a concentration of ethanol in the culture of that may be at most about 4%, 3.5%, 3%, 2.5%, 2%, 1.8%, 1.6%, 1.5%, 1.4%, 1.3%, 1.2%, 1.1%, 1.0%, 0.9%, 0.8%, 0.7%, 0.6%, 0.5%, 0.4%, 0.35%, 0.3%, 0.25%, 0.2%, or 0.15% (w/v).

The step of adding the ethanol bolus may comprise adding ethanol to said culture, adding a carrier comprising ethanol to said culture, adding said cells to a medium or carrier comprising ethanol, or replacing part of the culture medium.

Said desired protein may contain one or more polypeptides comprising at least one disulfide bond.

Said desired protein may comprise a multi-subunit complex.

Said multi-subunit complex may comprise an antibody.

The method may decrease the relative abundance of one or more product-associated variants relative to the same method effected in the absence of the temperature shift.

The method may decrease the relative abundance of product-associated variants having a higher or lower apparent molecular weight than said desired multi-subunit complex as detected by size exclusion chromatography or gel electrophoresis relative to the same method effected in the absence of the temperature shift.

The method may decrease the relative abundance of complexes having aberrant stoichiometry relative to the same method effected in the absence of the temperature shift.

The method may decrease the relative abundance of complexes having aberrant disulfide bonds relative to the same method effected in the absence of the temperature shift.

The method may comprise adding a feed to the eukaryotic cells.

The respiratory quotient (RQ) value may be maintained at a specified value or in a specified range. Said specified RQ value may be 1.12. Said specified RQ range may be, for example, 1.0 to 1.24, or 1.06 to 1.18, or 1.09 to 1.15.

The specified RQ value or range may be maintained by modulating (increasing or decreasing) one or more of the concentration of glucose, availability of oxygen, intensity of agitation, gas pressure, flow rate of supplied air or other gas mixture, viscosity of the culture, culture density, concentration of oxygen in the supplied air or other gas mixture, and temperature. For example, the rate of feed addition (feed rate) may be modulated (increased or decreased) in order to control the respiratory quotient (RQ), e.g., to maintain a specified RQ value or range.

Said feed may comprise at least one fermentable carbon source.

Said carbon source may comprise one or more of: glycerol, glucose, ethanol, citrate, sorbitol, xylose, trehalose, arabinose, galactose, fructose, melibiose, lactose, maltose, rhamnose, ribose, mannose, mannitol, and raffinose.

The genes that provide for expression of said desired protein may be integrated into one or more genomic loci.

At least one of said genomic loci may be selected from the group consisting of the pGAP locus, 3' AOX TT locus; PpURA5; OCH1; AOX1; HIS4; GAP; pGAP; 3' AOX TT; ARG; and the HIS4 TT locus.

At least one of the genes encoding said subunits of the multi-subunit complex may be expressed under control of an inducible or constitutive promoter.

Said inducible promoter may be selected from the group consisting of the AOX1, CUP, tetracycline inducible, thiamine inducible, and FLD1 promoters.

At least one of the genes encoding said subunits of the multi-subunit complex may be expressed under control of a promoter selected from the group consisting of: the CUP1, AOX1, ICL1, glyceraldehyde-3-phosphate dehydrogenase (GAP), FLD1, ADH1, alcohol dehydrogenase II, GAL4, PHO3, PHO5, and Pyk promoters, tetracycline inducible promoters, thiamine inducible promoters, chimeric promoters derived therefrom, yeast promoters, mammalian promoters, insect promoters, plant promoters, reptile promoters, amphibian promoters, viral promoters, and avian promoters.

Said eukaryotic cell may be a diploid, tetraploid cell, or polyploid.

The method may further comprise purifying said multi-subunit complex from said eukaryotic cells or from the culture medium.

Said multi-subunit complex may be purified from an intracellular component, cytoplasm, nucleoplasm, or a membrane of said eukaryotic cells.

Said eukaryotic cells secrete said desired protein into the culture medium.

Said desired protein may be purified from said culture medium.

Said desired protein may comprise a monospecific or bispecific antibody.

Said desired protein may comprise a human antibody or a humanized antibody or fragment thereof.

Said humanized antibody may be of mouse, rat, rabbit, goat, sheep, or cow origin.

Said humanized antibody may be of rabbit origin.

Said desired protein may comprise a monovalent, bivalent, or multivalent antibody.

Said antibody may be purified from said culture by protein A and/or protein G affinity.

At least one of the genes that provide for expression of said desired protein may be optimized for expression in said eukaryotic cell.

Said desired protein may comprise an antibody and the purity of said antibody may be assessed by measuring the fraction of the antibody produced by said eukaryotic cell that may be contained in antibody complexes having the expected apparent hydrodynamic radius, may be contained in antibody complexes having the expected molecular weight, and/or specifically binds a target of said antibody.

Said desired protein may comprise an antibody and the yield of said antibody may be assessed by determining the amount of antibody produced by said eukaryotic cell discounting any product-associated variants that may be abnormally glycosylated, contained in antibody complexes other than complexes having the expected apparent hydrodynamic radius, contained in antibody complexes having the expected molecular weight, and/or that fail to specifically bind to the target of said antibody.

The molecular weight of said antibody complexes may be determined by non-reducing SDS-PAGE.

Said desired protein may comprise an antibody, said method may further comprise purifying said antibody.

Said culture cell may produce a supernatant antibody titer of at least 100 mg/L, at least 150 mg/L, at least 200 mg/L, at least 250 mg/L, at least 300 mg/L, between 100 and 300 mg/L, between 100 and 500 mg/L, between 100 and 1000 mg/L, at least 1000 mg/L, at least 1250 mg/liter, at least 1500 mg/liter, at least about 1750 mg/liter, at least about 2000 mg/liter, at least about 10000 mg/liter, or more.

Said desired protein may comprise a multi-subunit complex and one or more subunits of said multi-subunit complex may be expressed from more than one gene copy.

Said desired protein may comprise an antibody which may be expressed from between 1-10 copies of a gene encoding the light chain of said antibody and from 1-10 copies of a gene encoding the heavy chain of said antibody.

The gene(s) that provide for expression of said desired protein may be integrated into genome of said cells.

The gene(s) that provide for expression of said desired protein may be contained on an extrachromosomal element, plasmid, or artificial chromosome.

Said cells may comprise more copies of the gene that provide for the expression of the light chain of said antibody than copies of the gene that provide for expression of the heavy chain of said antibody.

The respective number of copies of the gene encoding the heavy chain of said antibody and the number of copies of the gene encoding the light chain of said antibody in said cells may be: 2 and 2, 2 and 3, 3 and 3, 3 and 4, 3 and 5, 4 and 3, 4 and 4, 4 and 5, 4 and 6, 5 and 4, 5 and 5, 5 and 6, or 5 and 7.

The respective number of copies of the gene encoding the heavy chain of said antibody and the number of copies of the gene encoding the light chain of said antibody in said cells may be: 2 and 1, 3 and 1, 4 and 1, 5 and 1, 6 and 1, 7 and 1, 8 and 1, 9 and 1, 10 and 1, 1 and 2, 2 and 2, 3 and 2, 4 and 2, 5 and 2, 6 and 2, 7 and 2, 8 and 2, 9 and 2, 10 and 2, 1 and 3, 2 and 3, 3 and 3, 4 and 3, 5 and 3, 6 and 3, 7 and 3, 8 and 3, 9 and 3, 10 and 3, 1 and 4, 2 and 4, 3 and 4, 4 and 4, 5 and 4, 6 and 4, 7 and 4, 8 and 4, 9 and 4, 10 and 4, 1 and 5, 2 and 5, 3 and 5, 4 and 5, 5 and 5, 6 and 5, 7 and 5, 8 and 5, 9 and 5, 10 and 5, 1 and 6, 2 and 6, 3 and 6, 4 and 6, 5 and 6, 6 and 6, 7 and 6, 8 and 6, 9 and 6, 10 and 6, 1 and 7, 2 and 7, 3 and 7, 4 and 7, 5 and 7, 6 and 7, 7 and 7, 8 and 7, 9 and 7, 10 and 7, 1 and 8, 2 and 8, 3 and 8, 4 and 8, 5 and 8, 6 and 8, 7 and 8, 8 and 8, 9 and 8, 10 and 8, 1 and 9, 2 and 9, 3 and 9, 4 and 9, 5 and 9, 6 and 9, 7 and 9, 8 and 9, 9 and 9, 10 and 9, 1 and 10, 2 and 10, 3 and 10, 4 and 10, 5 and 10, 6 and 10, 7 and 10, 8 and 10, 9 and 10, 10 and 10.

Using the methods of the present disclosure, the relative abundance of undesired side-product(s) may be decreased by at least 10%, at least 20%, at least 30%, at least 40%, at least 50%, at least 60%, at least 70%, at least 80%, at least 90%, at least 95%, at least 96%, at least 97%, at least 98%, at least 99%, or down to undetectable levels compared to initial abundance levels, relative to conventional methods. Exemplary undesired side-products whose relative abundance may be so decreased may include one or more species having a different apparent molecular weight than the desired multi-subunit complex. For example, apparent molecular weight may be affected by differences in stoichiometry, folding, complex assembly, and/or glycosylation. For example, such undesired side products may be detected using size exclusion chromatography and/or gel electrophoresis, and may have a higher or lower apparent molecular weight than the desired multi-subunit complex. In exemplary embodiments, the undesired side-products may be detected under reducing conditions. In other exemplary embodiments, the undesired side-products may be detected under non-reducing conditions.

In exemplary embodiments, the present disclosure also provides improved methods and compositions of matter that provide for the recombinant production of antibodies and other multi-subunit complexes, with a higher yield. In exemplary embodiments, the yield may be increased by at least 10%, at least 20%, at least 30%, at least 40%, at least 50%, at least 100%, or more (relative to conventional methods) using the methods disclosed herein.

In exemplary embodiments, the eukaryotic cell in which the desired protein may be produced may be a yeast, for example in a *Pichia* species such as *P. pastoris* or another methylotrophic yeast, or in a *Saccharomyces* species such as *S. cerevisiae*, or another yeast such as a *Schizosaccharomyces* (e.g., *S. pombe*). Other examples of methylotrophic yeast which may be utilized in the present invention include *Pichia angusta* (also known in the art as *Hansenula polymorpha*), *Pichia guillermordii*, *Pichia methanolica*, *Pichia inositovera*, *Ogataea nitraloaversa*, and *Candida boidnii*.

The eukaryotic cell may be a yeast cell, such as a methylotrophic yeast, such as a yeast of the genus *Pichia*. Exemplary methylotrophic yeasts of the genus *Pichia* include *Pichia pastoris*, *Pichia angusta*, *Pichia guillermordii*, *Pichia methanolica*, and *Pichia inositovera*. The host cell may be produced by mating, e.g., by mating two haploid yeast cells that each contain one or more copies of at least one gene encoding a subunit of the multi-subunit complex.

In a preferred embodiment, the methylotrophic yeasts of the genus *Pichia* is *Pichia pastoris*. The eukaryotic cell may be a diploid or tetraploid cell.

At least one of the genes encoding said desired protein may be expressed under control of an inducible or constitutive promoter, such as CUP1 (induced by the level of copper in the medium; see Koller et al., Yeast 2000; 16: 651-656.), tetracycline inducible promoters (see, e.g., Staib et al., Antimicrobial Agents And Chemotherapy, January 2008, p. 146-156), thiamine inducible promoters, AOX1, ICL1, glyceraldehyde-3-phosphate dehydrogenase (GAP), FLD1, ADH1, alcohol dehydrogenase II, GAL4, PHO3, PHO5, and Pyk promoters, chimeric promoters derived therefrom, yeast promoters, mammalian promoters, insect promoters, plant promoters, reptile promoters, amphibian promoters, viral promoters, and avian promoters.

The eukaryotic cell may secrete said desired protein into the culture medium. For example, said desired protein may comprise a secretion signal peptide. Alternatively or in addition, said desired multi-subunit complex may be retained in said host cell and may be isolated therefrom.

The desired protein may comprise an antibody, such as a monospecific or bispecific antibody. The antibody may be an antibody that specifically binds any antigen.

The desired protein may comprise an antibody of any type. Exemplary antibody types include antibodies of any mammalian species, e.g., human, mouse, rat, rabbit, goat, sheep, cow, etc. Preferably, the antibody is a human antibody or a humanized antibody that may be of rabbit origin. The antibody may be a monovalent, bivalent, or multivalent antibody.

At least one of said genes that provide for expression of the desired protein, such as the light chain and/or heavy chain of a desired antibody, in said eukaryotic cell may be optimized for expression in said host cell (e.g., by selecting preferred codons and/or altering the percentage AT through codon selection).

The purity of said desired protein, such as a desired antibody, may be assessed by measuring the fraction of the desired protein produced by said host cell that is non-glycosylated, is contained in complexes having the expected apparent hydrodynamic radius and/or apparent molecular weight (e.g., measured by size exclusion chromatography), has the expected electrophoretic mobility (e.g., detected by gel electrophoresis, such as SDS-PAGE, and optionally Western blotting), and/or by measuring the specific activity of the multi-subunit complex (e.g., specific binding a target of a desired antibody).

The desired protein may be an antibody, and yield of said antibody may be assessed by determining the amount of desired antibody produced by said host cell discounting any product-associated variants that are glycosylated, contained in antibody complexes other than complexes having the expected apparent molecular weight or hydrodynamic radius, and/or that fail to specifically bind to the target of said desired antibody.

BRIEF DESCRIPTION OF THE DRAWINGS

FIG. 1 illustrates the beneficial effect of a culture temperature shift on recombinant antibody production. Whole broth ("WB") antibody titer (arbitrary units) is plotted against time points throughout fermentation for five different temperature shifts and an unshifted control (maintained at 28° C.). Pre-shift temperature was 28° C. and post-shift temperature was 25° C., 29.5° C., 31° C., 32.5° C., or 34° C. as indicated. Upward temperature shifts of between 1.5° C. and 3° C. (final temperature, 29.5° C. and 31° C., respectively) resulted in increased final titers. The antibody produced in these experiment was Ab-A. For the culture shifted to 31° C., the final titer was increased by about 30% relative to the unshifted control culture (maintained at 28° C.).

FIG. 2A-B summarizes purity of the recombinant antibodies produced with a culture temperature shift in FIG. 1. Purity was assessed by size exclusion chromatography of protein A-purified antibody harvested at the end of antibody production. Panel A shows the purity assessed under non-reducing conditions. Peaks were detected corresponding to the full antibody ("Main peak IgG") and two aberrant antibody complexes ("Prepeak HHL" and "75 kD HL"). Numbers shown are percentage of the total detected protein contained in each peak. A similar proportion of the total protein was contained in the main antibody peak for unshifted cultures (i.e., maintained at 28° C.) and cultures shifted to 29.5° C. and 31° C. Panel B shows purity detected under reduced conditions. For each temperature condition the percentage of total detected protein contained in the heavy chain ("HC"), light chain ("LC") and the total heavy and light chain protein ("Total HC+LC") is shown, along with the percentage contained in three other peaks ("RT 9.80," "RT 10.16," and "RT 10.80"). As compared to the unshifted culture maintained at 28° C., the percentage of protein contained in the heavy and light chain peaks remained similar for the culture shifted to 29.5° C. and was increased by about 4% for higher temperature shifts.

FIG. 3A-C details purity of the recombinant antibodies produced as shown in FIG. 1 for the culture shifted downward to 25° C. Panel A, size exclusion chromatography traces and tabulated results for non-reduced samples. Panel B, Coomassie stained gel electrophoresis results for non-reduced (lane 1) and reduced (lane 3) samples. Lanes 2 and 4 show a size marker. Panel 3, size exclusion chromatography traces and tabulated results for reduced samples. Chromatography results are tabulated and summarized in FIG. 2.

FIG. 4A-C details purity of the recombinant antibody as shown in FIG. 1 for the control culture produced without a temperature shift and maintained at 28° C. Panel A, size exclusion chromatography traces and tabulated results for non-reduced samples. Panel B, Coomassie stained gel electrophoresis results for non-reduced (lane 1) and reduced (lane 3) samples. Lanes 2 and 4 show a size marker. Panel 3, size exclusion chromatography traces and tabulated results for reduced samples. Chromatography results are tabulated and summarized in FIG. 2.

FIG. 5A-C details purity of the recombinant antibodies produced as shown in FIG. 1 for the culture shifted upward by 1.5° C. to 29.5° C. Panel A, size exclusion chromatography traces and tabulated results for non-reduced samples. Panel B, Coomassie stained gel electrophoresis results for non-reduced (lane 1) and reduced (lane 3) samples. Lanes 2 and 4 show a size marker. Panel 3, size exclusion chromatography traces and tabulated results for reduced samples. Chromatography results are tabulated and summarized in FIG. 2.

FIG. 6A-C details purity of the recombinant antibodies produced as shown in FIG. 1 for the culture shifted upward by 3° C. to 31° C. Panel A, size exclusion chromatography traces and tabulated results for non-reduced samples. Panel B, Coomassie stained gel electrophoresis results for non-reduced (lane 1) and reduced (lane 3) samples. Lanes 2 and 4 show a size marker. Panel 3, size exclusion chromatography traces and tabulated results for reduced samples. Chromatography results are tabulated and summarized in FIG. 2.

FIG. 7A-C details purity of the recombinant antibodies produced as shown in FIG. 1 for the culture shifted upward by 4.5° C. to 32.5° C. Panel A, size exclusion chromatography traces and tabulated results for non-reduced samples. Panel B, Coomassie stained gel electrophoresis results for non-reduced (lane 1) and reduced (lane 3) samples. Lanes 2 and 4 show a size marker. Panel 3, size exclusion chromatography traces and tabulated results for reduced samples. Chromatography results are tabulated and summarized in FIG. 2.

FIG. 8A-C details purity of the recombinant antibodies produced as shown in FIG. 1 for the culture shifted upward by 6° C. to 34° C. Panel A, size exclusion chromatography traces and tabulated results for non-reduced samples. Panel B, Coomassie stained gel electrophoresis results for non-reduced (lane 1) and reduced (lane 3) samples. Lanes 2 and 4 show a size marker. Panel 3, size exclusion chromatography traces and tabulated results for reduced samples. Chromatography results are tabulated and summarized in FIG. 2.

FIG. 9A-B shows improvement in titer of Ab-B resulting from a temperature shift during culture. Panel A: whole broth antibody titer (arbitrary units) is shown graphically versus time in culture of a high-expressing strain comprising 4 copies of the Ab-B heavy chain gene and 3 copies of the Ab-B light chain gene ("H4/L3"). The temperature-shifted culture ("H4/L3 30 C") exhibited a greater titer at all time-points than the two non-shifted cultures ("H4/L3 28 C"). The average final antibody titer was increased by about 28%. Panel B: whole broth antibody titer (arbitrary units) is shown graphically versus time in a culture of a lower-expressing strain comprising 3 copies of the Ab-B heavy chain gene and 3 copies of the Ab-B light chain gene ("H3/L3"). The temperature-shifted culture ("H3/L3 30 C") exhibited a greater titer than the average of the two non-shifted cultures ("H3/L3 28 C").

FIG. 10 summarizes the purity of the recombinant antibodies produced with a culture temperature shift as shown in FIG. 9. Purity was assessed by size exclusion chromatography of protein A-purified antibody harvested at the end of antibody production. Labels are as described in FIG. 2.

FIG. 11 shows improvement in titer of Ab-A resulting from a temperature shift during culture. Whole broth antibody titer (arbitrary units) is plotted versus time for cultures which were subjected to a temperature shift during culture or control cultures for which a temperature shift was not performed. Four cultures were shifted from 28° C. to 30° C. after initiating feed addition (label "30 C") and five control cultures were unshifted and maintained at 28° C. throughout culturing. Each of the shifted cultures exhibited higher titers than the non-shifted cultures. The average increase in titer resulting from the temperature shift was about 47%.

FIG. 12 summarizes the purity of the recombinant antibodies produced with a culture temperature shift as shown in FIG. 11. Purity was assessed by size exclusion chromatography of protein A-purified antibody harvested at the end of antibody production. Labels are as described in FIG. 2.

DETAILED DESCRIPTION

Figure 13:
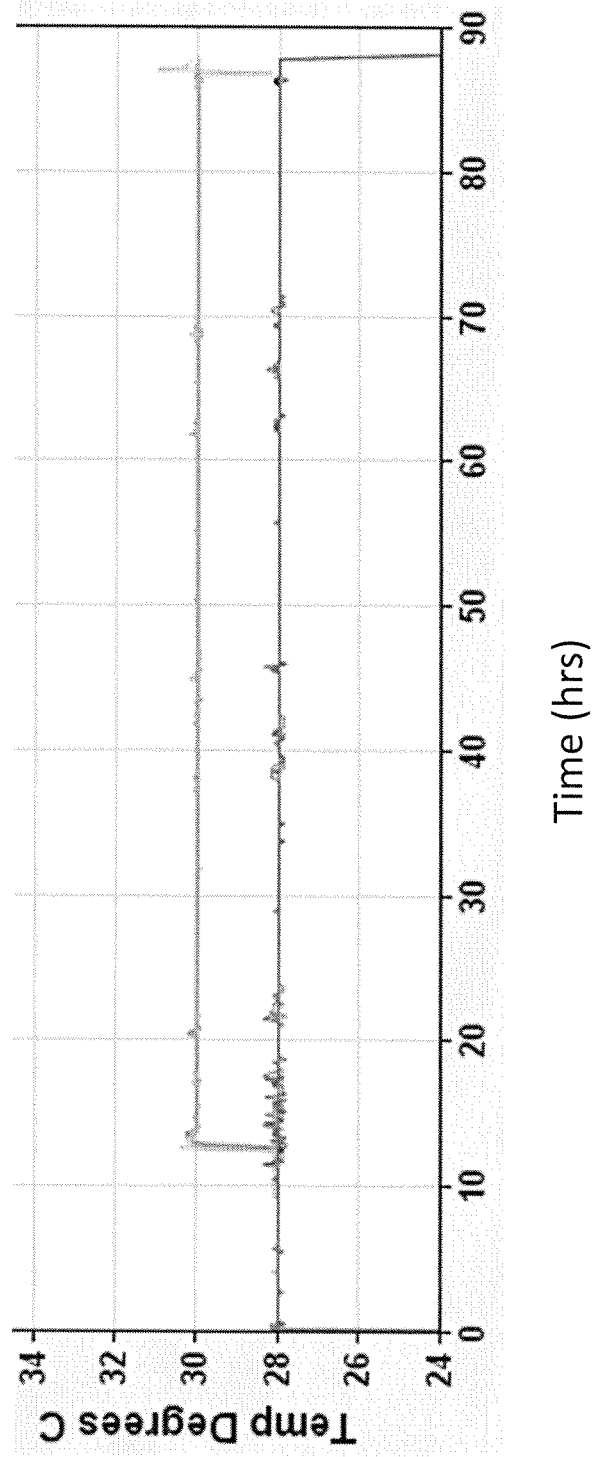
FIG. 13 shows the shows the temperature of each culture in example 3 plotted versus time in culture.

This disclosure describes methods of improving the yield and/or purity of recombinantly expressed proteins, including antibodies and other multi-subunit proteins. Methods are provided wherein a temperature shift is effected during cell culture. The inclusion of a temperature shift is demonstrated below to improve the yield and purity of recombinantly expressed antibodies, compared to expression in the absence of the shift.

Though not intending to be limited by theory, it is hypothesized that a temperature shift can cause sustained changes in gene expression which confer a lasting improvement in recombinant protein production. Said improvement may be mediated by improvements in protein expression, stability, folding, post-translational processing, and (in the case of antibodies and other multi-subunit complexes) proper subunit assembly, e.g., due to a sustained increase in expression of heat shock proteins.

Preferred host cells include yeasts, and particularly preferred yeasts include methylotrophic yeast strains, e.g., *Pichia pastoris, Hansenula polymorpha (Pichia angusta), Pichia guillermordii, Pichia methanolica, Pichia inositovera*, and others (see, e.g., U.S. Pat. Nos. 4,812,405, 4,818,700, 4,929,555, 5,736,383, 5,955,349, 5,888,768, and 6,258,559 each of which is incorporated by reference in its entirety). The host cell may be produced by methods known in the art, such as transformation, mating, sporulation, etc.

In exemplary embodiments, the disclosure provides methods which decrease the production of one or more undesired side products. Relative to the desired protein, the undesired side product(s) may exhibit one or more of: altered stoichiometry (in the case of a multi-subunit complex), aberrant glycosylation, differences in apparent molecular weight, differences in disulfide bonds, differences in hydrodynamic radius, fragments and/or truncations. Undesired side-products may exhibit one or more additional differences as well.

Undesired side-products may also be detected by their effects on a preparation, e.g., alteration in the level of specific activity, immunogenicity, or other effects on physical constitution and/or function of the desired multi-subunit complex.

For example, when the desired protein is an antibody, the undesired side products may include an H1L1 or "half antibody" species (i.e., containing a heavy chain and a light chain, wherein the heavy chain is not linked by a disulfide bond to another heavy chain), and/or a H2L1 species (i.e., containing two heavy chains and one light chain, but lacking a second light chain).

In a preferred embodiment, the host cell may comprise more than one copy of one or more of the gene encoding the desired protein or the genes encoding the subunits thereof. For example, multiple copies of a subunit gene may be integrated in tandem into one or more chromosomal loci. Tandemly integrated gene copies are preferably retained in a stable number of copies during culture for the production of the multi-subunit complex. For example, a co-owned application published as US 2013/0045888 describes experiments wherein gene copy numbers were generally stable for *P. pastoris* strains containing three to four tandemly integrated copies of light and heavy chain antibody genes.

One or more of the genes encoding the desired protein may be integrated into one or multiple chromosomal loci of a host cell. Any suitable chromosomal locus may be utilized for integration, including intergenic sequences, promoters sequences, coding sequences, termination sequences, regulatory sequences, etc. Exemplary chromosomal loci that may be used in *P. pastoris* include PpURA5; OCH1; AOX1; HIS4; and GAP. The encoding genes may also be integrated into one or more random chromosomal loci rather than being targeted. In exemplary embodiments, the chromosomal loci are selected from the group consisting of the pGAP locus, 3' AOX TT, and the HIS4 TT locus. In additional exemplary embodiments, the genes encoding the heterologous protein subunits may be contained in one or more extrachromosomal elements, for example one or more plasmids or artificial chromosomes.

In exemplary embodiments, the desired protein may be a multi-subunit complex comprising two, three, four, five, six, or more identical or non-identical subunits. Additionally, each subunit may be present one or more times in each multi-subunit protein. For example, the desired protein may comprise a multi-specific antibody such as a bi-specific antibody comprising two non-identical light chains and two non-identical heavy chains. As a further example, the desired protein may comprise an antibody comprising two identical light chains and two identical heavy chains.

The subunits may be expressed from monocistronic genes, polycistronic genes, or any combination thereof. Each polycistronic gene may comprise multiple copies of the same subunit, or may comprise one or more copies of each different subunit.

Exemplary methods that may be used for manipulation of *Pichia pastoris* (including methods of culturing, transforming, and mating) are disclosed in Published Applications including U.S. 20080003643, U.S. 20070298500, and U.S. 20060270045, and in Higgins, D. R., and Cregg, J. M., Eds. 1998. *Pichia* Protocols. Methods in Molecular Biology. Humana Press, Totowa, N.J., and Cregg, J. M., Ed., 2007, *Pichia* Protocols (2nd edition), Methods in Molecular Biology. Humana Press, Totowa, N.J., each of which is incorporated by reference in its entirety.

An exemplary expression cassette that may be utilized is composed of the glyceraldehyde dehydrogenase gene (GAP gene) promoter, fused to sequences encoding a secretion signal, followed by the sequence of the gene to be expressed, followed by sequences encoding a *P. pastoris* transcriptional termination signal from the *P. pastoris* alcohol oxidase I gene (AOX1). The Zeocin resistance marker gene may provide a means of enrichment for strains that contain multiple integrated copies of an expression vector in a strain by selecting for transformants that are resistant to higher levels of Zeocin. Similarly, G418 or Kanamycin resistance marker genes may be used to provide a means of enrichment for strains that contain multiple integrated copies of an expression vector in a strain by selecting for transformants that are resistant to higher levels of Geneticin or Kanamycin.

Host strains that may be utilized include auxotrophic *P. pastoris* or other *Pichia* strains, for example, strains having mutations in met1, lys3, ura3 and ade1 or other auxotrophy-associated genes. Preferred mutations are incapable of giving rise to revertants at any appreciable frequency and are preferably partial or even more preferably full deletion mutants. For example, prototrophic diploid or tetraploid strains are produced by mating a complementing sets of auxotrophic strains. Said strains have the advantage of being able to be grown on minimal media, and additionally said media tend to select against growth of haploid cells that may arise through sporulation.

Transformation of haploid and diploid *P. pastoris* strains and genetic manipulation of the *P. pastoris* sexual cycle may be performed as described in *Pichia* Protocols (1998, 2007), supra.

Prior to transformation, each expression vector may be linearized by restriction enzyme cleavage within a region homologous to the target genomic locus (e.g., the GAP promoter sequence) to direct the integration of the vectors into the target locus in the host cell. Samples of each vector may then be individually transformed into cultures of the desired strains by electroporation or other methods, and successful transformants may be selected by means of a selectable marker, e.g., antibiotic resistance or complementation of an auxotrophy. Isolates may be picked, streaked for single colonies under selective conditions and then examined to confirm the number of copies of the gene encoding the desired protein or subunit of the multi-subunit complex (e.g., a desired antibody) by Southern Blot or PCR assay on genomic DNA extracted from each strain. Optionally, expression of the expected subunit gene product may be confirmed, e.g., by FACS, Western Blot, colony lift and immunoblot, and other means known in the art. Optionally, isolates are transformed additional times to introduce additional heterologous genes, e.g., additional copies of the gene encoding a desired protein, or in the case of a multi-subunit protein, genes encoding the same subunit may be integrated at a different locus, and/or copies of a different subunit may be integrated. Strains may be produced as haploids, diploids, or other ploidies (including tetraploid and higher ploidies). Haploid strains may be produced and mated in order to rapidly test different combinations of gene copy numbers, e.g., numbers of copies of a single gene encoding a desired protein, or numbers of copies of the differing genes encoding the subunits of a multi-subunit protein. Presence of the desired protein gene or each expected subunit gene may be confirmed by Southern blotting, PCR, and other detection means known in the art. Additionally, expression of an antibody or other desired protein may also be confirmed by a colony lift/immunoblot method (Wung et al. Biotechniques 21 808-812 (1996) and/or by FACS.

Transformation is optionally repeated to target a heterologous gene into a second locus, which may be the same gene or a different gene than was targeted into the first locus. When the construct to be integrated into the second locus encodes a protein that is the same as or highly similar to the sequence encoded by the first locus, its sequence may be varied to decrease the likelihood of undesired integration into the first locus. Such sequence differences may also promote genetic stability by decreasing the likelihood of subsequent recombination events. For example, the sequence to be integrated into the second locus may have differences in the promoter sequence, termination sequence, codon usage, and/or other tolerable sequence differences relative to the sequence integrated into the first locus.

To mate *P. pastoris* haploid strains, each strain to be crossed can be patched together onto mating plates. For example, multiple matings can be conveniently performed at the same time by streaking each strain to be mated across a plate suitable for its growth, and the mating partners may be streaked across a second plate (preferably the plates are rich media such as YPD). Typically, after one or two days incubation at 30° C., cells from the two plates can be replica plated in a crisscross fashion onto a mating plate, resulting in a cross-hatched pattern with each pair of strains being co-plated and having the opportunity to mate at the intersection of a pair of the original streak lines. The mating plate can then be incubated (e.g., at 30° C.) to stimulate the initiation of mating between strains. After about two days, the cells on the mating plates can be streaked, patched, or replica plated onto media selective for the desired diploid strains (e.g., where the mated strains have complementary autotrophies, drop-out or minimal medium plates may be used). These plates can be incubated (e.g., at 30° C.) for a suitable duration (e.g., about three days) to allow for the selective growth of the desired diploid strains. Colonies that arise can be picked and streaked for single colonies to isolate and purify each diploid strain.

Expression vectors for use in the methods of the invention may further include yeast specific sequences, including a selectable auxotrophic or drug marker for identifying transformed yeast strains. A drug marker may further be used to amplify copy number of the vector in a yeast host cell, e.g., by culturing a population of cells in an elevated concentration of the drug, thereby selecting transformants that express elevated levels of the resistance gene.

In an exemplary embodiment, one or more of the genes encoding the heterologous protein subunits are coupled to an inducible promoter. Suitable exemplary promoters include the alcohol oxidase 1 gene promoter, formaldehyde dehydrogenase genes (FLD; see U.S. Pub. No. 2007/0298500), and other inducible promoters known in the art. The alcohol oxidase 1 gene promoter, is tightly repressed during growth of the yeast on most common carbon sources, such as glucose, glycerol, or ethanol, but is highly induced during growth on methanol (Tschopp et al., 1987; U.S. Pat. No. 4,855,231 to Stroman, D. W., et al). For production of foreign proteins, strains may be initially grown on a repressing carbon source to generate biomass and then shifted to methanol as the sole (or main) carbon and energy source to induce expression of the foreign gene. One advantage of this regulatory system is that *P. pastoris* strains transformed with foreign genes whose expression products are toxic to the cells can be maintained by growing under repressing conditions.

In another exemplary embodiment, one or more of the heterologous genes may be coupled to a regulated promoter, whose expression level can be upregulated under appropriate conditions. Exemplary regulated promoters include the CUP1 promoter (induced by the level of copper in the medium), tetracycline inducible promoters, thiamine inducible promoters, the AOX1 promoter, and the FLD1 promoter.

Though much of the present disclosure describes production of antibodies, the methods described herein are readily adapted to other desired proteins including single subunit and multi-subunit proteins. Additionally, the present methods are not limited to production of multi-protein complexes but may also be readily adapted for use with ribonucleoprotein (RNP) complexes including telomerase, hnRNPs, Ribosomes, snRNPs, signal recognition particles, prokaryotic and eukaryotic RNase P complexes, and any other complexes that contain multiple distinct protein and/or RNA subunits. The host cell that expresses a multi-subunit complex may be produced by methods known in the art. For example, a panel of diploid or tetraploid yeast cells containing differing combinations of gene copy numbers may be generated by mating cells containing varying numbers of copies of the individual subunit genes (which numbers of copies preferably are known in advance of mating).

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Bolus addition: In the present disclosure, "bolus addition" generally refers to rapid change in concentration of a substance (such as ethanol) in contact with cultured cells (for example, in a culture medium). For example, the substance may be added to the cultured cells in a single addition, a succession of more than one addition, and/or infused over a period of time (e.g., over about 1, 2, 3, 4, 5, 6, 7, 8, 9, 10, 15, 20, 25, 30, 40, 50, 60, 90, or 120 minutes). The substance may also be added by replacing the culture medium in part or in full, for example by concentrating the cells (using centrifugation, filtration, settling, or other methods), removing part or all of the medium, and adding the substance, or by adding the cells to a medium containing the substance. The substance may be admixed with a carrier (e.g., culture media, water, saline, etc.). For example, a bolus addition of ethanol may comprise the addition of pure or concentrated ethanol (e.g., 100%, 95%, 70%, 50%, 60%, 40%, 30%, 20%, etc.) to the culture medium in an amount sufficient to produce the desired concentration. As another example, the cells may be added to a medium containing ethanol, e.g., by adding an inoculum containing the cells to a medium containing ethanol.

Bolus concentration: In the present disclosure, "bolus concentration" generally refers to the concentration that results from a bolus addition of a substance (e.g., ethanol).

Mating competent yeast species: In the present invention this is intended to broadly encompass any diploid or tetraploid yeast which can be grown in culture. Such species of yeast may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or fusion (e.g., spheroplast fusion).

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia; Rhodosporidium; Candida; Hansenula; Filobasium; Sporidiobolus; Bullera; Leucosporidium* and *Filobasidella*.

In a preferred embodiment of the invention, the mating competent yeast is a member of the genus *Pichia* or is another methylotroph. In a further preferred embodiment of the invention, the mating competent yeast of the genus *Pichia* is one of the following species: *Pichia pastoris, Pichia methanolica*, and *Hansenula polymorpha* (*Pichia angusta*). In a particularly preferred embodiment of the invention, the mating competent yeast of the genus *Pichia* is the species *Pichia pastoris*.

Haploid Yeast Cell: A cell having a single copy of each gene of its normal genomic (chromosomal) complement.

Polyploid Yeast Cell: A cell having more than one copy of its normal genomic (chromosomal) complement.

Diploid Yeast Cell: A cell having two copies (alleles) of essentially every gene of its normal genomic complement, typically formed by the process of fusion (mating) of two haploid cells.

Tetraploid Yeast Cell: A cell having four copies (alleles) of essentially every gene of its normal genomic complement, typically formed by the process of fusion (mating) of two diploid cells. Tetraploids may carry two, three, four, or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his] can be mated with the diploid [arg] to obtain a tetraploid prototroph. It will be understood by those of skill in the art that reference to the benefits and uses of diploid cells may also apply to tetraploid cells.

Yeast Mating: The process by which two yeast cells fuse to form a single yeast cell. The fused cells may be haploid cells or cells of higher ploidy (e.g., mating two diploid cells to produce a tetraploid cell).

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example, through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two temperature sensitive ("ts") mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; NEO (G418); LYS3; MET1; MET3a; ADE1; ADE3; URA3; and the like.

Integrated: A genetic element (typically a heterologous genetic element) that are covalently joined into a chromosome of an organism.

Tandemly integrated: Two or more copies of a genetic element that are integrated in adjacent locations in a chromosome. The two or more copies do not necessarily have the orientation; e.g., for transcribed genes, some copies may be transcribed from the Watson strand and others from the Crick strand.

Host cell: In the context of the present disclosure, the term host cell refers to a cell (e.g., a eukaryotic cell, such as a *Pichia* cell) which contains a heterologous gene. For example, the heterologous gene may provide for the expression of a subunit of a desired multi-subunit complex, a gene involved in protein folding (e.g., a chaperone), expression, or secretion, and/or another desired gene. The heterologous gene may be integrated into the genome of the eukaryotic cell or contained in extrachromosomal element such as a plasmid or artificial chromosome.

The respiratory quotient (RQ), is defined as the number of moles of $CO_2$ produced divided by the number of moles of $O_2$ consumed. For the complete oxidation of carbohydrates, the RQ value is 1.0. Fermentation is indicated by RQ values greater than one, and with no or low $O_2$ utilization (e.g., for metabolism in the absence of molecular oxygen) RQ may reach very large or theoretically infinite values.

Expression Vector: These DNA vectors contain elements that facilitate manipulation for the expression of a foreign protein within the target host cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press, which is incorporated by reference herein in its entirety.

Expression vectors for use in the methods of the invention may further include yeast specific sequences, including a selectable auxotrophic or drug marker for identifying transformed yeast strains. A drug marker may further be used to select for amplification of copy number of the vector in a yeast host cell.

The polypeptide coding sequence of interest is typically operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome.

Though optional, in one embodiment of the invention, the desired protein or a subunit of the desired multi-subunit complex is operably linked, or fused, to a secretion sequence that provides for secretion of the expressed polypeptide into the culture media, which can facilitate harvesting and purification of the desired protein or complex. Even more preferably, the secretion sequences provide for optimized secretion of the polypeptide from the host cells (e.g., yeast diploid cells), such as through selecting preferred codons and/or altering the percentage AT through codon selection. It is known in the art that secretion efficiency and/or stability can be affected by the choice of secretion sequence and the optimal secretion sequence can vary between different proteins (see, e.g., Koganesawa et al., Protein Eng. 2001 September; 14(9):705-10, which is incorporated by reference herein in its entirety). Many potentially suitable secretion signals are known in the art and can readily be tested for their effect upon yield and/or purity of a particular desired protein or complex. Any secretion sequences may potentially be used, including those present in secreted proteins of yeasts and other species, as well as engineered secretion sequences. Exemplary secretion signal sequences that may be utilized include: chicken lysozyme (CLY) signal peptide (MRSLLILVLCFLPLAALG (SEQ ID NO:414)), CLY-L8 (MRLLLLLLLLPLAALG (SEQ ID NO:415)), *S. cerevisiae* invertase (SUC2) signal peptide (MLLQAFLFL-LAGFAAKISA (SEQ ID NO:416)), MF-alpha (Prepro) (MRFPSIFTAVLFAASSALA-APVNTTTE-EGVSLEKR (SEQ ID NO:417)), MF-alpha (Pre)-apv (MRFPSIFTAVL-FAASSALA-APV (SEQ ID NO:418)), MF-alpha (Pre)-apv-SLEKR (MRFPSIFTAVLFAASSALA-APVSLEKR (SEQ ID NO:419)), MF-alpha (Prepro)-(EA)3 (MRFPSIFTAVL-FAASSALA-APVNTTTE-EGVSLEKR-EAEAEA (SEQ ID NO:420)), αF signal peptide (MRFPSIFTAVLFAAS-SALA-APVNTTTE-DETAQIPAEAVIGYSDLEGDFDVA-VLPFSNSTNNGLLFINTTIASIAAKE-EGVSLEKR (SEQ ID NO:421)), KILM1 signal peptide (MTKPTQVLVRSVSILFFITLLHLVVALNDVAG-PAETAPVSLLPR (SEQ ID NO:422)), repressible acid phosphatase (PHO1) signal peptide (MFSPILSLEIILA-LATLQSVFA (SEQ ID NO:423)), *A. niger* GOX signal peptide (MQTLLVSSLVVSLAAALPHYIR (SEQ ID NO:424)), *Schwanniomyces occidentalis* glucoamylase gene (GAM 1) signal peptide (MIFLKLIKSIVIGLGLVSAIQA (SEQ ID NO:425)), human serum albumin (HSA) signal peptide with pro-sequence (MKWVTFISLLFLFSSAY-SRGVFRR (SEQ ID NO:426)), human serum albumin (HSA) signal peptide without pro-sequence (MKWVTFIS-LLFLFSSAYS (SEQ ID NO:427)), ISN signal peptide (MALWMRLLPLLALLALWGPDPAAA (SEQ ID NO:428)), IFN signal peptide (MKYTSYILAFQL-CIVLGSLGCDLP (SEQ ID NO:429)), HGH signal peptide (MAADSQTPWLLTFSLLCLLWPQEPGA (SEQ ID NO:430)), phytohaemagglutinin (PHA) (MKKNRMMM-MIWSVGVVWMLLLVGGSYG (SEQ ID NO:431)), Silkworm lysozyme (MQKLIIFALVVLCVGSEA (SEQ ID NO:432)), Human lysozyme (LYZ1) (MKAL- IVLGLVLLSVTVQG (SEQ ID NO:433)), activin receptor type-1 (MVDGVMILPVLIMIALPSPS (SEQ ID NO:434)), activin type II receptor (MGAAAKLAFAVFLISCSSG (SEQ ID NO:435)), *P. pastoris* immunoglobulin binding protein (PpBiP) (MLSLKPSWLTLAALMYAMLLVVVP-FAKPVRA (SEQ ID NO:436)), and human antibody 3D6 light chain leader (MDMRVPAQLLGLLLLWLPGAKC (SEQ ID NO:437)). See Hashimoto et al., Protein Engineering vol. 11 no. 2 pp. 75-77, 1998; Oka et al., Biosci Biotechnol Biochem. 1999 November; 63(11):1977-83; Gellissen et al., FEMS Yeast Research 5 (2005) 1079-1096; Ma et al., Hepatology. 2005 December; 42(6):1355-63; Raemaekers et al., Eur J Biochem. 1999 Oct. 1; 265(1):394-403; Koganesawa et al., Protein Eng. (2001) 14 (9): 705-710; Daly et al., Protein Expr Purif. 2006 April; 46(2):456-67; Damasceno et al., Appl Microbiol Biotechnol (2007) 74:381-389; and Felgenhauer et al., Nucleic Acids Res. 1990 Aug. 25; 18(16):4927, each of which is incorporated by reference herein in its entirety).

The desired protein or complex may also be secreted into the culture media without being operably linked or fused to a secretion signal. For example, it has been demonstrated that some heterologous polypeptides are secreted into the culture media when expressed in *P. pastoris* even without being linked or fused to a secretion signal. Additionally, the desired protein or multi-subunit complex may be purified from host cells (which, for example, may be preferable if the complex is poorly secreted) using methods known in the art.

Media or cells comprising a desired protein or multi-subunit complex may be recovered from the culture. Optionally, the secreted proteins may be purified. For example, cells comprising a desired protein or multi-subunit complex may be lysed using mechanical, chemical, enzymatic, and/or osmotic methods (e.g., freezing with liquid nitrogen, using a homogenizer, spheroplasting, sonication, agitation in the presence of glass beads, using detergents, etc.). The desired protein or multi-subunit complex may be concentrated, filtered, dialyzed, etc., using methods known in the art. The desired protein or multi-subunit complex may be purified based on, for example, its molecular mass (e.g., size exclusion chromatography), isoelectric point (e.g., isoelectric focusing), electrophoretic mobility (e.g., gel electrophoresis), hydrophobic interaction chromatography (e.g., HPLC), charge (e.g., ion exchange chromatography), affinity (e.g., in the case of an antibody, binding to protein A, protein G, and/or an epitope to which the desired antibody binds), and/or glycosylation state (e.g., detected by lectin binding affinity). Multiple purification steps may be performed to obtain the desired level of purity. In an exemplary embodiment, the desired protein or multi-subunit complex may be comprise an immunoglobulin constant domain and may be purified using protein A or protein G affinity, size exclusion chromatography, and lack of binding to lectin (to remove glycosylated forms). Optionally the A protease inhibitor, such as phenyl methyl sulfonyl fluoride (PMSF) may be added to inhibit proteolytic degradation during purification.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking may be accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers may be used in accordance with conventional practice. Desired nucleic acids (including nucleic acids comprising operably linked sequences) may also be produced by chemical synthesis.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. *Pichia* transformation is described in Cregg et al. (1985) Mol. Cell. Biol. 5:3376-3385, which is incorporated by reference herein in its entirety.

Examples of suitable promoters from *Pichia* include the CUP1 (induced by the level of copper in the medium), tetracycline inducible promoters, thiamine inducible promoters, AOX1 promoter (Cregg et al. (1989) Mol. Cell. Biol. 9:1316-1323); ICL1 promoter (Menendez et al. (2003) Yeast 20(13):1097-108); glyceraldehyde-3-phosphate dehydrogenase promoter (GAP) (Waterham et al. (1997) Gene 186(1): 37-44); and FLD1 promoter (Shen et al. (1998) Gene 216(1):93-102). The GAP promoter is a strong constitutive promoter and the CUP1, AOX and FLD1 promoters are inducible. Each foregoing reference is incorporated by reference herein in its entirety.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 pre-protoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998), each of which is incorporated by reference herein in its entirety.

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and E. coli-encoded recombination proteins. Recombination occurs between specific attachment (att) sites on the interacting DNA molecules. For a description of att sites see Weisberg and Landy (1983) Site-Specific Recombination in Phage Lambda, in Lambda II, Weisberg, ed. (Cold Spring Harbor, N.Y.: Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology. Each foregoing reference is incorporated by reference herein in its entirety.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Monocistronic and polycistronic genes. A monocistronic gene encodes an RNA that contains the genetic information to translate only a single protein. A polycistronic gene encodes an mRNA that contains the genetic information to translate more than one protein. The proteins encoded in a polycistronic gene may have the same or different sequences or a combination thereof. Dicistronic or bicistronic refers to a polycistronic gene that encodes two proteins. Polycistronic genes optionally include one or more internal ribosome entry site (IRES) elements to facilitate cap-independent initiation of translation, which may be situated at a location that can drive translation of the downstream protein coding region independently of the 5'-cap structure bound to the 5' end of the mRNA molecule. Any known IRES sequence (e.g., viral, eukaryotic, or artificial in origin) may be used. For example, the cricket paralysis virus IRES sequence in the intergenic region (IGR) may be used, as described in Thompson et al. (2001) PNAS 98:12972-12977. Optionally, IRES function may be potentiated by genetic alteration, e.g., by causing constitutive expression of eIF2 kinase GCN2 or disrupting two initiator tRNA(met) genes disrupted (id.).

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, PDI, BIP, cyclophilin, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, the multi-subunit complex may be expressed from a yeast strain produced by mating, wherein each of the haploid parental strains expresses a distinct folding enzyme, e.g. one strain may express BIP, and the other strain may express PDI or combinations thereof.

The terms "desired protein" or "target protein" are used interchangeably and refer generally to a heterologous multi-subunit protein such as an antibody (e.g., a humanized antibody) or a binding portion thereof described herein.

The term "antibody" includes any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies such as scFvs, camelbodies, nanobodies, IgNAR (single-chain antibodies derived from sharks), small-modular immunopharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73; Nuttall S D, et al., Isolation of the new antigen receptor from wobbegong sharks, and use as a scaffold for the display of protein loop libraries, Mol Immunol. 2001 August; 38(4): 313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19. Each foregoing reference is incorporated by reference herein in its entirety.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, or IgG4 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference. Methods of humanizing antibodies have been described previously in issued U.S. Pat. No. 7,935,340, the disclosure of which is incorporated herein by reference in its entirety. In some instances, a determination of whether additional rabbit framework residues are required to maintain activity is necessary. In some instances the humanized antibodies still requires some critical rabbit framework residues to be retained to minimize loss of affinity or activity. In these cases, it is necessary to change single or multiple framework amino acids from human germline sequences back to the original rabbit amino acids in order to have desired activity. These changes are determined experimentally to identify which rabbit residues are necessary to preserve affinity and activity.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

Product-associated variant: a product other than the desired product (e.g., the desired multi-subunit complex) which is present in a preparation of the desired product and related to the desired product. Exemplary product-associated variants include truncated or elongated peptides, products having different glycosylation than the desired glycosylation (e.g., if an aglycosylated product is desired then any glycosylated product would be considered to be a product-associated variant), complexes having abnormal stoichiometry, improper assembly, abnormal disulfide linkages, abnormal or incomplete folding, aggregation, protease cleavage, or other abnormalities. Exemplary product-associated variants may exhibit alterations in one or more of molecular mass (e.g., detected by size exclusion chromatography), isoelectric point (e.g., detected by isoelectric focusing), electrophoretic mobility (e.g., detected by gel electrophoresis), phosphorylation state (e.g., detected by mass spectrometry), charge to mass ratio (e.g., detected by mass spectrometry), mass or identity of proteolytic fragments (e.g., detected by mass spectrometry or gel electrophoresis), hydrophobicity (e.g., detected by HPLC), charge (e.g., detected by ion exchange chromatography), affinity (e.g., in the case of an antibody, detected by binding to protein A, protein G, and/or an epitope to which the desired antibody binds), and glycosylation state (e.g., detected by lectin binding affinity). Where the desired protein is an antibody, the term product-associate variant may include a glyco-heavy variant and/or half antibody species (described below).

Exemplary product-associated variants include variant forms that contain aberrant disulfide bonds. For example, most IgG1 antibody molecules are stabilized by a total of 16 intra-chain and inter-chain disulfide bridges, which stabilize the folding of the IgG domains in both heavy and light chains, while the inter-chain disulfide bridges stabilize the association between heavy and light chains. Other antibody types likewise contain characteristic stabilizing intra-chain and inter-chain disulfide bonds. Further, some antibodies (including Ab-A and Ab-B disclosed herein) contain additional disulfide bonds referred to as non-canonical disulfide bonds. Thus, aberrant inter-chain disulfide bonds may result in abnormal complex stoichiometry, due to the absence of a stabilizing covalent linkage, and/or disulfide linkages to additional subunits. Additionally, aberrant disulfide bonds (whether inter-chain or intra-chain) may decrease structural stability of the antibody, which may result in decreased activity, decreased stability, increased propensity to form aggregates, and/or increased immunogenicity. Product-associated variants containing aberrant disulfide bonds may be detected in a variety of ways, including non-reduced denaturing SDS-PAGE, capillary electrophoresis, ciEX, mass spectrometry (optionally with chemical modification to produce a mass shift in free cysteines), size exclusion chromatography, HPLC, changes in light scattering, and any other suitable methods known in the art. See, e.g., The Protein Protocols Handbook 2002, Part V, 581-583, DOI: 10.1385/1-59259-169-8:581;

Half antibody, half-antibody species, or HIL1 refer to a protein complex that includes a single heavy and single light antibody chain, but lacks a covalent linkage to a second heavy and light antibody chain. Two half antibodies may remain non-covalently associated under some conditions, but may be separated under appropriate conditions (e.g., detergent, salt, or temperature) to facilitate their detection separate from full H2L2 antibodies. Similarly, H2L1 refers to a protein complex that includes two heavy antibody chains and single light antibody chain, but lacks a covalent linkage to a second light antibody chain; these complexes may also non-covalently associate with another light antibody chain (and likewise give similar behavior to a full antibody). Like full antibodies, half antibody species and H2L1 species can dissociate under reducing conditions into individual heavy and light chains. Half antibody species and H2L1 species can be detected on a non-reduced SDS-PAGE gel as a species migrating at a lower apparent molecular weight than the full antibody, e.g., HIL1 migrates at approximately half the apparent molecular weight of the full antibody (e.g., about 75 kDa).

Glyco-heavy variant refers to a glycosylated product-associated variant sometimes present in antibody preparations and which contains at least a partial Fc sequence. The glyco-heavy variant is characterized by decreased electrophoretic mobility observable by SDS-PAGE (relative to a normal heavy chain), lectin binding affinity, binding to an anti-Fc antibody, and apparent higher molecular weight of antibody complexes containing the glyco-heavy variant as determined by size exclusion chromatography. See U.S. Provisional Application Ser. No. 61/525,307, filed Aug. 31, 2011 which is incorporated by reference herein in its entirety.

The term "polyploid yeast that stably expresses or expresses a desired secreted heterologous polypeptide for prolonged time" refers to a yeast culture that secretes said polypeptide for at least several days to a week, more preferably at least a month, still more preferably at least 1-6 months, and even more preferably for more than a year at threshold expression levels, typically at least 50-500 mg/liter (after about 90 hours in culture) and preferably substantially greater.

The term "polyploidal yeast culture that secretes desired amounts of recombinant polypeptide" refers to cultures that stably or for prolonged periods secrete at least at least 50-500 mg/liter, and most preferably 500-1000 mg/liter or more.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in the following review articles, each of which is incorporated by reference herein in its entirety: Van Brunt 1990, Bio/Technol., 8(4):291-294; and Gill and Ghaemi, Nucleosides Nucleotides Nucleic Acids. 2008 March; 27(3):224-43. Polymerase chain reaction or PCR is a prototype of nucleic acid amplification, and use of PCR herein should be considered exemplary of other suitable amplification techniques.

The general structure of antibodies in most vertebrates (including mammals) is now well understood (Edelman, G. M., Ann. N.Y. Acad. Sci., 190: 5 (1971)). Conventional antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to gamma, mu, alpha, delta, and epsilon heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either kappa or lambda. Each heavy chain class can be paired with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

The expression "stable copy number" refers to a host cell that substantially maintains the number of copies of a gene (such as an antibody chain gene) over a prolonged period of time (such as at least a day, at least a week, or at least a month, or more) or over a prolonged number of generations of propagation (e.g., at least 30, 40, 50, 75, 100, 200, 500, or 1000 generations, or more). For example, at a given time point or number of generations, at least 50%, and preferably at least 70%, 75%, 85%, 90%, 95%, or more of cells in the culture may maintain the same number of copies of the gene as in the starting cell. In a preferred embodiment, the host cell contains a stable copy number of the gene encoding the desired protein or encoding each subunit of the desired multi-subunit complex (e.g., antibody).

The expression "stably expresses" refers to a host cell that maintains similar levels of expression of a gene or protein (such as an antibody) over a prolonged period of time (such as at least a day, at least a week, or at least a month, or more) or over a prolonged number of generations of propagation (e.g., at least 30, 40, 50, 75, 100, 200, 500, or 1000 generations, or more). For example, at a given time point or number of generations, the rate of production or yield of the gene or protein may be at least 50%, and preferably at least 70%, 75%, 85%, 90%, 95%, or more of the initial rate of production. In a preferred embodiment, the host cell stably expresses the desired protein or multi-subunit complex (e.g., antibody).

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

This example tests the effect of a temperature shift on yield and purity of antibodies expressed from *P. pastoris*. Antibody yield was increased by up to about 30% by an upward temperature shift effected during culture. Additionally, purity was increased by the temperature shift, as indicated by a decrease in the abundance of product-associated variants and aberrant complexes.

Methods

Ab-A was expressed from a *P. pastoris* strain containing 4 integrated copies of the heavy chain gene and 3 integrated copies of the light chain gene (SEQ ID NOS: 1 and 2, respectively). An inoculum was expanded using a medium comprised of the following nutrients (% w/v): yeast extract 3%, glycerol 2%, YNB 1.34%, Biotin 0.004% and 27.2 g/l potassium phosphate monobasic. To generate the inoculum for the fermenters, the cells were grown for approximately 24-28 hours in a shaking incubator at 30° C. and 300 rpm.

The Ab-A sequences are as follows:
Ab-A Heavy Chain Polynucleotide Sequence:

(SEQ ID NO: 1)
gaggtgcagcttgtggagtctgggggaggcttggtccagcctgggggtc cctgagactctcctgtgcagtctctggaatcgacctcagtggctactaca tgaactgggtccgtcaggctccagggaaggggctggagtgggtcggagtc attggtattaatggtgccacatactacgcgagctgggcgaaaggccgatt caccatctccagagacaattccaagaccacggtgtatcttcaaatgaaca gcctgagagctgaggacactgctgtgtatttctgtgctagaggggacatc tggggccaagggaccctcgtcaccgtctcgagcgcctccaccaagggccc atcggtcttcccctggcaccctcctccaagagcacctctgggggcacagc ggccctgggctgcctggtcaaggactacttccccgaaccggtgacggtgt cgtggaactcaggcgccctgaccagcggcgtgcacaccttcccggctgtc ctacagtcctcaggactctactccctcagcagcgtggtgaccgtgccctc cagcagcttgggcacccagacctacatctgcaacgtgaatcacaagccca gcaacaccaaggtggacgcgagagttgagcccaaatcttgtgacaaaact cacacatgcccaccgtgcccagcacctgaactcctggggggaccgtcagt cttcctcttccccccaaaacccaaggacacccctcatgatctcccggaccc ctgaggtcacatgcgtggtggtggacgtgagccacgaagaccctgaggtc aagttcaactggtacgtggacggcgtggaggtgcataatgccaagacaaa gccgcgggaggagcagtacgccagcacgtaccgtgtggtcagcgtcctca ccgtcctgcaccaggactggctgaatggcaaggagtacaagtgcaaggtc tccaacaaagccctcccagcccccatcgagaaaaccatctccaaagccaa agggcagccccgagaaccacaggtgtacaccctgcccccatcccgggagg agatgaccaagaaccaggtcagcctgacctgcctggtcaaaggcttctat cccagcgacatcgccgtggagtgggagagcaatgggcagccggagaacaa ctacaagaccacgcctcccgtgctggactccgacggctccttcttcctct acagcaagctcaccgtggacaagagcaggtggcagcaggggaacgtcttc tcatgctccgtgatgcatgaggctctgcacaaccactacacgcagaagag cctctccctgtctccgggtaaatga Ab-A Light Chain Polynucleotide Sequence:

(SEQ ID NO: 2)
caagtgctgacccagtctccatcctccctgtctgcatctgtaggagacag agtcaccatcaattgccaggccagtcagagtgtttatcataacacctacc tggcctggtatcagcagaaaccagggaaagttcctaagcaactgatctat gatgcatccactctggcatctggggtcccatctcgtttcagtggcagtgg atctgggacagatttcactctcaccatcagcagcctgcagcctgaagatg ttgcaacttattactgtctgggcagttatgattgtactaatggtgattgt tttgttttcggcggaggaaccaaggtggaaatcaaacgtacggtggctgc accatctgtcttcatcttcccgccatctgatgagcagttgaaatctggaa ctgcctctgttgtgtgcctgctgaataacttctatcccagagaggccaaa gtacagtggaaggtggataacgccctccaatcgggtaactcccaggagag tgtcacagagcaggacagcaaggacagcacctacagcctcagcagcaccc tgacgctgagcaaagcagactacgagaaacacaaagtctacgcctgcgaa gtcacccatcagggcctgagctcgcccgtcacaaagagcttcaacagggg agagtgttag A 10% inoculum was then added to Applikon 17L working volume vessels containing 6 L sterile growth medium. The growth medium was comprised of the following nutrients: potassium sulfate 18.2 g/L, ammonium phosphate monobasic 35.6 g/L, potassium phosphate dibasic 12.8 g/L, magnesium sulfate heptahydrate 3.72 g/L, sodium citrate dihydrate 10 g/L, glycerol 40 g/L, yeast extract 30 g/L, PTM1 trace metals 4.35 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L. The bioreactor process control parameters were set as follows: Agitation 950 rpm, airflow 1.35 standard liter per minute, temperature 28° C. and pH was controlled (at 6) using ammonium hydroxide. No oxygen supplementation was provided.

Fermentation cultures were grown for approximately 12 to 16 hours at 28° C. until the initial glycerol was consumed, which was detected by a rapid increase in the concentration of dissolved oxygen, referred to as the DO spike. Immediately after the DO spike was detected, a bolus of 11 grams of 100% ethanol per liter of culture was added to the reactor to attain a final concentration of about 1.1% ethanol (w/v). The fermentation cultures were allowed to equilibrate for 20 minutes. Feed addition was then initiated at a constant rate of 11 g glucose/L/hr for the duration of the fermentation. Approximately 8 hrs after the feed addition was initiated, RQ control was initiated using agitation feed back control with a minimum agitation speed of 500 rpm and a maximum agitation speed of 950 rpm thereby maintaining the RQ set point of 1.12 for the remainder of the fermentation. The feed was comprised of the following components: yeast extract 50 µL, dextrose anhydrous 500 g/L, magnesium sulfate heptahydrate 3 g/L, and PTM1 trace metals 12 mL/L. Optionally, sodium citrate dihydrate (1.66 g/L) was also added to the feed. Feed pH was 6.0.

Five minutes after feed initiation, the culture temperature was rapidly shifted to one of five different temperatures (25° C., 29.5° C., 31° C., 32.5° C., and 34° C.). Additionally, a control culture was maintained at 28° C., i.e., without temperature shift. The total fermentation time was approximately 86-87 hours.

Samples were collected from each culture throughout the fermentation and whole broth titers were determined and were plotted in arbitrary units which are consistent among the figures in this application. Additionally, at the end of the run, antibody purity was determined (after Protein A purification) by size-exclusion chromatography (SE-HPLC) performed on reduced and non-reduced samples using an Agilent (Santa Clara, Calif.) 1200 Series HPLC with UV detection instrument. For sample separation, a TSKgel GS3000SWx1 7.8×300 mM column connected with a TSK-gel Guard SWx1 6×40 mM from Tosoh Bioscience (King of Prussia, Pa.) was used. A 100 mM sodium phosphate, 200 mM sodium chloride pH 6.5 was used as mobile phase with a flow rate of 0.5 mL/min in isocratic mode and absorbance at UV 215 nm was monitored. Before injection of samples the column was equilibrated until a stable baseline was achieved. Samples were diluted to a concentration of 1 mg/mL using mobile phase and a 30 µL volume was injected. To monitor column performance, BioRad (Hercules, CA) gel filtration standards were used.

Results

*P. pastoris* engineered to express Ab-A was grown in cultures maintained at 28° C. during an initial growth phase with glycerol as a carbon source. After exhaustion of the glycerol, a continuous glucose feed was initiated and the culture temperature was rapidly shifted upward or downward to a new set-point temperature between 25° C. and 34° C. which was maintained for the duration of the culture. One culture was maintained at 28° C. as a control.

To monitor antibody production, culture media (into which the antibody was secreted due to inclusion of a secretion signal) was periodically sampled up to the final time-point of 86-87 hours. Whole broth antibody titer (arbitrary units) was determined and is shown graphically for each culture temperature in FIG. 1. As depicted, the highest final titer was achieved for the culture maintained at 31° C. A slightly higher titer was initially obtained for the culture maintained at 32.5° C., however the whole broth titer leveled off and began to decrease between 65-70 hours, and the final titer was lower than was observed for the non-shifted culture. The second-highest final titer was observed with the culture maintained at 29.5° C. The culture shifted up to 34° C. and the culture shifted downward to 25° C. both produced titers lower than the culture maintained at 28° C.

Additionally, antibody purity at the end of culture (i.e., at 86-87 hours) was determined. Specifically, protein-A purified antibody from each culture was assessed by exclusion chromatography (SEC) and by gel electrophoresis with Coomassie staining (FIGS. 3-8), which were conducted for both reduced and non-reduced samples. SEC analysis of non-reduced samples detected relative abundance of complexes having aberrant stoichiometry, including a 75 kDA "half antibody" species containing a single heavy chain and a single light chain, and a "HHL" complex containing two heavy chains and a single light chain. SEC analysis of reduced samples detected relative abundance of intact heavy and light chains as well as aberrant subunits having an elution time of approximately 9.8, 10.15, and 10.8 minutes (which are thought to correspond to glycosylated forms of the antibody heavy chain).

The SEC results are summarized in FIG. 2A-B. The non-reduced SEC analysis demonstrated that a similar proportion of the total protein was contained in the main antibody peak for unshifted cultures (i.e., maintained at 28° C.) and cultures shifted to 29.5° C. and 31° C., with all three conditions maintaining 88-89% of total protein within the full antibody peak (FIG. 2A). Thus, with respect to misassembled complexes, the upward shift to 29.5° C. and 31° C. did not adversely affect purity. Further, the reduced SEC analysis demonstrated that compared to the unshifted culture, the proportion of total protein contained in the heavy and light chain peaks remained similar for the culture shifted to 29.5° C. and was increased by about 4% for higher temperature shifts.

Based thereon, it is concluded that upward temperature shifts to 29.5° C. or 31° C. (i.e., by 1.5° C. to 3° C.) increased final antibody yield. Additionally, purity was increased in the culture shifted to 31° C., while purity was not adversely affected for the culture shifted to 29.5° C.

Example 2

This example tests the effect of a temperature shift on yield and purity of antibodies expressed from *P. pastoris*. Two different strains were tested, a lower- and higher-producing strain. For the higher-producing strain, antibody yield was increased by about 28% by an upward temperature shift effected during culture. Based thereon it is concluded that production from an already highly optimized strain was substantially benefited by the temperature shift. Additionally, purity was increased by the temperature shift, as indicated by a decrease in the abundance of product-associated variants in most instances.

Methods

Ab-B was expressed from a *P. pastoris* strain containing 3 or 4 integrated copies of the heavy chain gene and 3 integrated copies of the light chain gene (SEQ ID NOS: 3 and 4, respectively. An inoculum was expanded using a medium comprised of the following nutrients (% w/v): yeast extract 3%, glycerol 2%, YNB 1.34%, Biotin 0.004% and 27.2 g/l potassium phosphate monobasic. To generate the inoculum for the fermenters, the cells were grown for approximately 24-28 hours in a shaking incubator at 30° C. and 300 rpm.

The Ab-B sequences are as follows:
Ab-B Heavy Chain Polynucleotide Sequence:

(SEQ ID NO: 3)
gaggtgcagctggtggagtctgggggaggcttggtccagcctgggggtc cctgagactctcctgtgcagcctctggattctccctcagtaactactacg tgacctgggtccgtcaggctccagggaaggggctggagtgggtcggcatc atctatggtagtgatgaaaccgcctacgctacctccgctataggccgatt caccatctccagagacaattccaagaacaccctgtatcttcaaatgaaca gcctgagagctgaggacactgctgtgtattactgtgctagagatgatagt agtgactgggatgcaaagttcaacttgtggggccaagggaccctcgtcac cgtctcgagcgcctccaccaagggcccatcggtcttccccctggcaccct cctccaagagcacctctgggggcacagcggccctgggctgcctggtcaag gactacttccccgaaccggtgacggtgtcgtggaactcaggcgccctgac cagcggcgtgcacaccttcccggctgtcctacagtcctcaggactctact ccctcagcagcgtggtgaccgtgccctccagcagcttgggcacccagacc tacatctgcaacgtgaatcacaagcccagcaacaccaaggtggacaagag agttgagcccaaatcttgtgacaaaactcacacatgcccaccgtgcccag cacctgaactcctggggggaccgtcagtcttcctcttccccccaaaaccc aaggacaccctcatgatctcccggacccctgaggtcacatgcgtggtggt ggacgtgagccacgaagaccctgaggtcaagttcaactggtacgtggacg gcgtggaggtgcataatgccaagacaaagccgcgggaggagcagtacgcc agcacgtaccgtgtggtcagcgtcctcaccgtcctgcaccaggactggct gaatggcaaggagtacaagtgcaaggtctccaacaaagccctcccagccc ccatcgagaaaaccatctccaaagccaaagggcagccccgagaaccacag gtgtacaccctgcccccatcccgggaggagatgaccaagaaccaggtcag cctgacctgcctggtcaaaggcttctatcccagcgacatcgccgtggagt gggagagcaatgggcagccggagaacaactacaagaccacgcctcccgtg ctggactccgacggctccttcttcctctacagcaagctcaccgtggacaa gagcaggtggcagcaggggaacgtcttctcatgctccgtgatgcatgagg ctctgcacaaccactacacgcagaagagcctctccctgtctccgggtaaa Ab-B Light Chain Polynucleotide Sequence:

(SEQ ID NO: 4)
gctatccagatgacccagtctccttcctccctgtctgcatctgtaggaga cagagtcaccatcacttgccaggccagtcagagcattaacaatgagttat cctggtatcagcagaaaccagggaaagcccctaagctcctgatctataagg gcatccactctggcatctggggtcccatcaaggttcagcggcagtggatc tgggacagacttcactctcaccatcagcagcctgcagcctgatgattttg caacttattactgccaacagggttatagtctgaggaacattgataatgct ttcggcggagggaccaaggtggaaatcaaacgtacggtggctgcaccatc tgtcttcatcttcccgccatctgatgagcagttgaaatctggaactgcct ctgttgtgtgcctgctgaataacttctatcccagagaggccaaagtacag tggaaggtggataacgccctccaatcgggtaactcccaggagagtgtcac agagcaggacagcaaggacagcacctacagcctcagcagcaccctgacgc tgagcaaagcagactacgagaaacacaaagtctacgcctgcgaagtcacc catcagggcctgagctcgcccgtcacaaagagcttcaacaggggagagt
gt A 10% inoculum was then added to Applikon 17L working volume vessels containing 6 L sterile growth medium. The growth medium was comprised of the following nutrients: potassium sulfate 18.2 g/L, ammonium phosphate monobasic 35.6 g/L, potassium phosphate dibasic 12.8 g/L, magnesium sulfate heptahydrate 3.72 g/L, sodium citrate dihydrate 10 g/L, glycerol 40 g/L, yeast extract 30 g/L, PTM1 trace metals 4.35 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L. The bioreactor process control parameters were set as follows: Agitation 950 rpm, airflow 1.35 standard liter per minute, temperature 28° C. and pH was controlled (at 6) using ammonium hydroxide. No oxygen supplementation was provided.

Fermentation cultures were grown for approximately 12 to 16 hours at 28° C. until the initial glycerol was consumed, which was detected by a rapid increase in the concentration of dissolved oxygen, referred to as the DO spike. Feed addition was then initiated at a rate of 15 g glucose/l/hr for 8 hrs. Approximately 8 hrs after feed addition was initiated, the feed addition rate was decreased to 13 g glucose/l/hr for the duration of the fermentation. Also, RQ control was initiated at this time using agitation feedback control with a minimum agitation of 500 rpm and a maximum agitation of 950 rpm to maintain a RQ set point of 1.12. The feed was comprised of the following components: yeast extract 50 g/L, dextrose anhydrous 500 g/L, magnesium sulfate heptahydrate 3 g/L, and PTM1 trace metals 12 mL/L. Optionally, sodium citrate dihydrate (1.66 g/L) was also added to the feed.

After feed initiation, the culture temperature was rapidly shifted to 30° C. for one culture of each of the two expressing strains. Additionally, for two cultures of each of the two strains, control cultures were maintained at 28° C., i.e., without temperature shift. The total fermentation time was approximately 86 hours.

Samples were collected from each culture throughout the fermentation and whole broth titers were determined and were plotted in arbitrary units which are consistent among the figures in this application. Additionally, at the end of the run, antibody purity was determined (after Protein A purification) by size-exclusion chromatography (SE-HPLC) using the methods described in Example 1.

Results

Ab-B was expressed from engineered *P. pastoris* strains containing 3 copies of the light chain-encoding gene and 3 copies of the heavy chain-encoding gene (H3/L3) or 3 copies of the light chain-encoding gene and 4 copies of the heavy chain-encoding gene (H4/L3). Cultures were initially grown at 28° C. with glycerol as a carbon source. After exhaustion of the glycerol, a continuous glucose feed was initiated and the culture temperature was rapidly shifted upward to 30° C. which was maintained for the duration of the culture, or maintained at 28° C. as a control.

At baseline, the H4/L3 strain (FIG. 9A) expressed a higher antibody titer than the H3/L3 strain (FIG. 9B), with the average final whole broth titer for unshifted cultures (i.e., maintained at 28° C.) being 12% higher for the H4/L3 strain.

The H4/L3 culture shifted to 30° C. exhibited a further 28% increase in final titer (relative to the average titer from the two H4/L3 cultures maintained at 28° C., i.e., without a shift). For the H3/L3 strains, the observed increase in final yield was somewhat less pronounced, however, the yield from the H3/L3 strain shifted to 30° C. increased by about 5% relative to the average final yield from two H3/L3 cultures maintained at 28° C. (i.e., without a shift).

FIG. 13 shows the temperature of each culture plotted versus time in culture. As expected, upon the temperature shift the cells rapidly reached the new set point temperature of 30° C., and both the shifted and unshifted cultures maintained their set point temperatures throughout the culture.

Antibody purity was also assessed from each culture using SE-HPLC. As described in Example 1, the non-reduced samples permitted detection of abundance of aberrant complexes (the 75 kDa "half-antibody" containing one heavy and one light chain and the HHL complex containing two heavy chains but only one light chain). The fraction of protein contained in the full antibody ("Main peak IgG") was increased for the two samples shifted to 30° C. compared to the average of their respective unshifted controls, which resulted from a decrease in both the 75 kDA HL species and Prepeak HHL species in the shifted samples relative to the average of the unshifted samples. Specifically, for the unshifted H4/L3 sample the average fraction of protein contained in the full antibody peak was 74.39%, in the Prepeak HHL was 4.26%, and the 75 kD HL was 12.65%, compared to 83.44%, 4.75%, and 6.15% for the shifted H4/L3 sample, respectively. Likewise for the unshifted H3/L3 samples the average fraction of protein contained in the full antibody peak was 82.80%, in the Prepeak HHL was 5.31%, and the 75 kD HL was 4.76%, compared to 91.63%, 2.94%, and 1.44%, respectively. In conclusion, the non-reducing SEC analysis demonstrated that the temperature shift (1) increased the average amount of antibody contained in the full antibody peak, and (2) decreased the average amount of the aberrant complexes in three out of four instances.

Also as described in Example 1, the reduced samples permitted detection of the relative abundance of protein contained in the full-length heavy and light chains as well as product-associated variants which were observed in three discrete elution peaks. Unlike the observed decrease in aberrant complexes observed with the non-reduced analysis, the reduced samples did not show a consistent improvement in the amount of antibody contained in the full-length heavy and light chains. Overall, for the two strains the average relative abundance of the heavy chain was increased by about 1-3% in the shifted cultures compared to the average of the unshifted cultures, and the average relative abundance of the light chain was unchanged or decreased by about 0.9% for the two strains.

Example 3

This example tests the effect of a temperature shift on yield and purity of antibodies expressed from *P. pastoris*. Antibody yield was increased by 47% on average by an upward temperature shift effected during culture.

Methods

Ab-A was expressed from a *P. pastoris* strain containing 4 integrated copies of the heavy chain gene and 3 integrated copies of the light chain gene as described in Example 1, except that five cultures were maintained at 28° C. (i.e., unshifted) and four cultures were shifted to 30° C. As in Example 1, the temperate shift was effected, if at all, at a time five minutes after feed initiation. The total fermentation time was approximately 87 hours.

Using the method described in Example 1, samples were collected from each culture throughout the fermentation and whole broth titers were determined and were plotted in arbitrary units which are consistent among the figures in this application, and antibody purity was determined for each culture at the final time point (after Protein A purification) by size-exclusion chromatography (SE-HPLC) performed on reduced and non-reduced samples.

Results

*P. pastoris* engineered to express Ab-A was grown in cultures maintained at 28° C. during an initial growth phase with glycerol as a carbon source. After exhaustion of the glycerol, a continuous glucose feed was initiated and the culture temperature was rapidly shifted upward to a new set-point of 28° C. which was maintained for the duration of the culture (N=4). Five control cultures were maintained at 28° C. (i.e., nonshifted).

Whole broth antibody titer was determined by periodic sampling and is shown graphically in FIG. 1I (arbitrary units). As depicted, each of the four cultures that were shifted to 30° C. produced a higher final titer than all of the nonshifted cultures maintained at 28° C. On average, the final titer was 47% higher for the shifted cultures than non-shifted cultures.

Additionally, purity was assessed by SE-HLPC and compared for the shifted and non-shifted cultures. The non-reduced samples revealed an approximately 2% increase in the relative amount of protein contained in the main antibody peak on average, with the prepeak HHL being reduced on average by about 21% and the 75 kDa HL peak being increased by 57%. The reduced samples revealed an across-the-board improvement in purity and decrease in average relative abundance of all three impurity peaks. Specifically relative to the non-shifed samples, the shifted samples exhibited a 26% decrease in the RT 9.80 peak, a 74% decrease in the RT 10.16 peak, and a 70% decrease in the RT 10.80 peak. In conclusion, the non-reducing SEC analysis demonstrated that the temperature shift (1) increased the average amount of antibody contained in the full antibody peak, and (2) decreased the average amount of two out of three aberrant complexes. The reduced SEC analysis revealed large decreases in relative abundance of each of the three detected impurity peaks.

Based thereon, it is concluded that an upward temperature shifts from 28° C. to 30° C. (i.e., by 2° C.) reproducibly increased final antibody yield by an average of 25-30%. Furthermore the purity of the antibodies as reflected by Capillary Electrophoresis Analysis also reflected an increase in purity in the temperature shifted cultures when compared to unshifted cultures, more noted in the reduced comparisons.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

The invention may be practiced in ways other than those particularly described in the foregoing description and examples. Numerous modifications and variations of the invention are possible in light of the above teachings and, therefore, are within the scope of the appended claims.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

Certain teachings related to methods for obtaining a clonal population of antigen-specific B cells were disclosed in U.S. Provisional patent application No. 60/801,412, filed May 19, 2006, and U.S. Patent Application Pub. No. 2012/0141982, the disclosure of each of which is herein incorporated by reference in its entirety.

Certain teachings related to humanization of rabbit-derived monoclonal antibodies and preferred sequence modifications to maintain antigen binding affinity were disclosed in International Application No. PCT/US2008/064421, corresponding to International Publication No. WO/2008/144757, entitled "Novel Rabbit Antibody Humanization Methods and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US2006/0270045), the disclosure of which is herein incorporated by reference in its entirety.

The entire disclosure of each document cited herein (including patents, patent applications, journal articles, abstracts, manuals, books, or other disclosures), including each document cited in the Background, Summary, Detailed Description, and Examples, is hereby incorporated by reference herein in its entirety.

What is claimed is:

1. A method of producing a desired full-length antibody, wherein the expression of the desired full-length antibody occurs in both step (a) and step (b) comprising:
   (a) wherein step (a) comprises culturing *Pichia pastoris* yeast cells comprising genes that provide for the expression of said desired full-length antibody at a first temperature which is between 27 degrees C. and 30 degrees C. inclusive; and
   (b) after step (a), step (b) comprises culturing the same *Pichia pastoris* yeast cells which are cultured in step (a) at a second temperature which is between 1 degree C. and 3 degrees C. inclusive higher than said first temperature and allowing said same culture of *Pichia pastoris* yeast cells to continue to produce said desired full-length antibody;
   wherein
   (i) culture step (a) and step (b) are effected after an inoculum expansion step;
   (ii) said desired full-length antibody is expressed under control of a non-temperature inducible promoter;
   (iii) said *Pichia pastoris* yeast cells comprise between 1-10 copies of a gene encoding the heavy chain of said desired full-length antibody and between 1-10 copies of a gene encoding the light chain of said desired full-length antibody;
   (iv) culture steps (a) and (b) comprise a batch phase followed by a fed batch phase, wherein culture step (a) is initiated during the batch phase and culture step (b) is initiated during the batch phase, during of the fed batch phase, or between the batch phase and the fed batch phase;
   (v) culture step (a) and step (b) comprise detecting a concentration of dissolved oxygen in the culture of *Pichia pastoris* yeast cells;
   (vi) said second temperature is effected after a rapid increase in the concentration of dissolved oxygen is detected in the culture; and (vii) said method increases the yield of said desired full-length antibody and/or decreases the relative abundance of full-length antibody complexes having aberrant disulfide bonds relative to the same culture method effected without a difference between said first temperature and said second temperature.

2. The method of claim 1, wherein: (i) said first temperature is between 27 degrees C. and 28.5 degrees C. or (ii) said first temperature is between 27.5 degrees C. and 28.5 degrees C. inclusive.

3. The method of claim 1, wherein;
(i) said method further decreases the relative abundance of one or more product-associated variants relative to the same method effected without a difference between said first temperature and said second temperature; and/or
(ii) said method decreases the relative abundance of product-associated variants having a higher or lower apparent molecular weight than said desired multi-subunit complex as detected by size exclusion chromatography or gel electrophoresis relative to the same method effected without a difference between said first temperature and said second temperature and/or
(iii) said method decreases the relative abundance of complexes having aberrant disulfide bonds relative to the same method effected without a difference between said first temperature and said second temperature; and/or
(iv) said method decreases the relative abundance of complexes having reduced cysteines relative to the same method effected without a difference between said first temperature and said second temperature; and/or
(v) said method decreases the relative abundance of complexes having aberrant glycosylation relative to the same method effected without a difference between said first temperature and said second temperature.

4. The method of claim 1, wherein said *Pichia pastoris* yeast cells comprise polyploidal *Pichia pastoris* yeast cells.

5. The method of claim 4, wherein the genes that provide for expression of said desired full-length antibody are integrated into one or more genomic loci.

6. The method of claim 1, wherein step (a) comprises culturing said *Pichia pastoris* yeast cells in a culture medium comprising glycerol as a carbon source until said glycerol is exhausted.

7. The method of claim 1, wherein said desired full-length antibody is expressed under control of a promoter selected from the group consisting of: the CUP I, AOX1, ICLI, glyceraldehyde-3-phosphate dehydrogenase (GAP), FLDI, ADH1, alcohol dehydrogenase II, GAL4, PHO3, PHO5, and Pyk promoters, tetracycline inducible promoters, thiamine inducible promoters, chimeric promoters derived therefrom, yeast promoters, mammalian promoters, insect promoters, plant promoters, reptile promoters, amphibian promoters, viral promoters, and avian promoters.

8. The method of claim 1, wherein said yeast cell is a diploid, tetraploid, or polyploid *Pichia pastoris* cell.

9. The method of claim 1, further comprising purifying said desired full-length antibody from said *Pichia pastoris* yeast cells or from the culture medium or from an intracellular component, cytoplasm, nucleoplasm, or a membrane of said yeast cells.

10. The method of claim 1, wherein said batch phase comprises culturing the yeast cell in a medium comprising a carbon source.

11. The method of claim 10, wherein the end of said batch phase is determined by exhaustion of the carbon source in the culture medium.

12. The method of claim 1, wherein the respiratory quotient (RQ) is maintained at a specified value or in a specified range during step (b), wherein (i) said specified RQ value is 1.12 or (ii) said specified RQ range is 1.0 to 1.24, or 1.06 to 1.18, or 1.09 to 1.15, or (iii) said RQ value or RQ range is maintained by modulating one or more of the feed rate, feed composition, supplied air flow rate, agitation rate, and/or oxygen concentration of supplied air.

13. The method of claim 1, wherein said first temperature is between 27.5° C. and 28.5° C. inclusive, and said second temperature is between 30° C. and 31° C inclusive.

14. The method of claim 11, wherein initiation of said second temperature is effected after a rapid increase in the concentration of dissolved oxygen is detected in the culture during the batch phase, during of the fed batch phase, or between the batch phase and the fed batch phase.

15. The method of claim 1, wherein said second temperature is (i) between 30 degrees C. and 33 degrees C. inclusive or (ii) said second temperature is between 30 degrees C. and 32 degrees C. inclusive or (iii) said second temperature is between 30 degrees C. and 31.5 degrees C. inclusive or (iv) said second temperature is between 30 degrees C. and 31 degrees C. inclusive.

16. The method of claim 1 wherein the respective number of copies of the gene encoding the heavy chain of said antibody and the number of copies of the gene encoding the light chain of said antibody in said cells may be: 2 and 2, 2 and 3, 3 and 3, 3 and 4, 3 and 5, 4 and 3, 4 and 4, 4 and 5, 4 and 6, 5 and 4, 5 and 5, 5 and 6, or 5 and 7.

17. The method of claim 1 wherein the respective number of copies of the gene encoding the heavy chain of said antibody and the number of copies of the gene encoding the light chain of said antibody in said cells may be: 2 and 1, 3 and 1, 4 and 1, 5 and 1, 6 and 1, 7 and 1, 8 and 1, 9 and 1, 10 and 1, 1 and 2, 2 and 2, 3 and 2, 4 and 2, 5 and 2, 6 and 2, 7 and 2, 8 and 2, 9 and 2, 10 and 2, 1 and 3, 2 and 3, 3 and 3, 4 and 3, 5 and 3, 6 and 3, 7 and 3, 8 and 3, 9 and 3, 10 and 3, 1 and 4, 2 and 4, 3 and 4, 4 and 4, 5 and 4, 6 and 4, 7 and 4, 8 and 4, 9 and 4, 10 and 4, 1 and 5, 2 and 5, 3 and 5, 4 and 5, 5 and 5, 6 and 5, 7 and 5, 8 and 5, 9 and 5, 10 and 5, 1 and 6, 2 and 6, 3 and 6, 4 and 6, 5 and 6, 6 and 6, 7 and 6, 8 and 6, 9 and 6, 10 and 6, 1 and 7, 2 and 7, 3 and 7, 4 and 7, 5 and 7, 6 and 7, 7 and 7, 8 and 7, 9 and 7, 10 and 7, 1 and 8, 2 and 8, 3 and 8, 4 and 8, 5 and 8, 6 and 8, 7 and 8, 8 and 8, 9 and 8, 10 and 8, 1 and 9, 2 and 9, 3 and 9, 4 and 9, 5 and 9, 6 and 9, 7 and 9, 8 and 9, 9 and 9, 10 and 9, 1 and 10, 2 and 10, 3 and 10, 4 and 10, 5 and 10, 6 and 10, 7 and 10, 8 and 10, 9 and 10, 10 and 10.

18. The method of claim 1, wherein said first temperature is 28 degrees C. and said second temperature is 30 degrees C. or 31 degrees C.

* * * * *

SEQUENCE LISTING

<160> NUMBER OF SEQ ID NOS: 28

<210> SEQ ID NO 1
<211> LENGTH: 1326
<212> TYPE: DNA
<213> ORGANISM: Artificial
<220> FEATURE:
<223> OTHER INFORMATION: Engineered antibody sequence

<400> SEQUENCE: 1

```
gaggtgcagc ttgtggagtc tgggggaggc ttggtccagc ctgggggtc cctgagactc      60 tcctgtgcag tctctggaat cgacctcagt ggctactaca tgaactgggt ccgtcaggct     120
ccagggaagg ggctggagtg ggtcggagtc attggtatta atggtgccac atactacgcg     180
agctgggcga aaggccgatt caccatctcc agagacaatt ccaagaccac ggtgtatctt     240
caaatgaaca gcctgagagc tgaggacact gctgtgtatt tctgtgctag aggggacatc     300
tggggccaag gaccctcgt caccgtctcg agcgcctcca ccaagggccc atcggtcttc     360
cccctggcac cctcctccaa gagcacctct gggggcacag cggccctggg ctgcctggtc     420
aaggactact ccccgaacc ggtgacggtg tcgtggaact caggcgccct gaccagcggc     480
gtgcacacct tcccggctgt cctacagtcc tcaggactct actccctcag cagcgtggtg     540
accgtgccct ccagcagctt gggcacccag acctacatct gcaacgtgaa tcacaagccc     600
agcaacacca aggtggacgc gagagttgag cccaaatctg tgacaaaac tcacacatgc     660 ccaccgtgcc cagcacctga actcctgggg ggaccgtcag tcttcctctt ccccccaaaa     720
cccaaggaca cctcatgat ctcccggacc cctgaggtca catgcgtggt ggtggacgtg     780
agccacgaag accctgaggt caagttcaac tggtacgtgg acggcgtgga ggtgcataat     840
gccaagacaa agccgcggga ggagcagtac gccagcacgt accgtgtggt cagcgtcctc     900
accgtcctgc accaggactg gctgaatggc aaggagtaca agtgcaaggt ctccaacaaa     960
gccctcccag cccccatcga gaaaccatc tccaaagcca aagggcagcc ccgagaacca    1020
```

```
caggtgtaca ccctgcccc  atcccggag  gagatgacca agaaccaggt cagcctgacc    1080
tgcctggtca aaggcttcta tcccagcgac atcgccgtgg agtgggagag caatgggcag    1140
ccggagaaca actacaagac cacgcctccc gtgctggact ccgacggctc cttcttcctc    1200
tacagcaagc tcaccgtgga caagagcagg tggcagcagg gaacgtctt  ctcatgctcc    1260 gtgatgcatg aggctctgca aaccactac  acgcagaaga gcctctccct gtctccgggt    1320
aaatga                                                              1326
```

<210> SEQ ID NO 2
<211> LENGTH: 660
<212> TYPE: DNA
<213> ORGANISM: Artificial
<220> FEATURE:
<223> OTHER INFORMATION: Engineered antibody sequence

<400> SEQUENCE: 2

```
caagtgctga cccagtctcc atcctccctg tctgcatctg taggagacag agtcaccatc     60
aattgccagg ccagtcagag tgtttatcat aacacctacc tggcctggta tcagcagaaa    120
ccagggaaag ttcctaagca actgatctat gatgcatcca ctctggcatc tggggtccca    180
tctcgtttca gtggcagtgg atctgggaca gatttcactc tcaccatcag cagcctgcag    240
cctgaagatg ttgcaactta ttactgtctg ggcagttatg attgtactaa tggtgattgt    300
tttgttttcg gcggaggaac caaggtggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
```

<210> SEQ ID NO 3
<211> LENGTH: 1350
<212> TYPE: DNA
<213> ORGANISM: Artificial
<220> FEATURE:
<223> OTHER INFORMATION: Engineered antibody sequence

<400> SEQUENCE: 3

```
gaggtgcagc tggtggagtc tgggggaggc ttggtccagc ctggggggtc cctgagactc     60
tcctgtgcag cctctggatt ctccctcagt aactactacg tgacctgggt ccgtcaggct    120
ccagggaagg ggctggagtg ggtcggcatc atctatggta gtgatgaaac cgcctacgct    180
acctccgcta taggccgatt caccatctcc agagacaatt ccaagaacac cctgtatctt    240
caaatgaaca gcctgagagc tgaggacact gctgtgtatt actgtgctag atgatagt     300 agtgactggg atgcaaagtt caacttgtgg ggccaaggga ccctcgtcac cgtctcgagc    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
```

```
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacgcc      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc      1020
aaagccaaag gcagccccg agaaccacag gtgtacaccc tgcccccatc ccggaggag        1080 atgaccaaga accaggtcag cctgacctgc ctggtcaaag gcttctatcc cagcgacatc      1140
gccgtggagt gggagagcaa tgggcagccg gagaacaact acaagaccac gcctcccgtg      1200
ctggactccg acggctcctt cttcctctac agcaagctca ccgtggacaa gagcaggtgg      1260
cagcagggga acgtcttctc atgctccgtg atgcatgagg ctctgcacaa ccactacacg      1320
cagaagagcc tctccctgtc tccgggtaaa                                      1350
```

```
<210> SEQ ID NO 4
<211> LENGTH: 651
<212> TYPE: DNA
<213> ORGANISM: Artificial
<220> FEATURE:
<223> OTHER INFORMATION: Engineered antibody sequence

<400> SEQUENCE: 4
```

```
gctatccaga tgacccagtc tccttcctcc ctgtctgcat ctgtaggaga cagagtcacc       60
atcacttgcc aggccagtca gagcattaac aatgagttat cctggtatca gcagaaacca      120
gggaaagccc ctaagctcct gatctatagg gcatccactc tggcatctgg ggtcccatca      180
aggttcagcg gcagtggatc tgggacagac ttcactctca ccatcagcag cctgcagcct      240
gatgattttg caacttatta ctgccaacag ggttatagtc tgaggaacat tgataatgct      300
ttcggcggag ggaccaaggt ggaaatcaaa cgtacggtgg ctgcaccatc tgtcttcatc      360
ttcccgccat ctgatgagca gttgaaatct ggaactgcct ctgttgtgtg cctgctgaat      420
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaag tctacgcctg cgaagtcacc      600
catcagggcc tgagctcgcc cgtcacaaag agcttcaaca ggggagagtg t              651
```

```
<210> SEQ ID NO 5
<211> LENGTH: 18
<212> TYPE: PRT
<213> ORGANISM: Artificial
<220> FEATURE:
<223> OTHER INFORMATION: Secretion peptide

<400> SEQUENCE: 5

Met Arg Ser Leu Leu Ile Leu Val Leu Cys Phe Leu Pro Leu Ala Ala
1               5                   10                  15

Leu Gly
```

```
<210> SEQ ID NO 6
<211> LENGTH: 16
<212> TYPE: PRT
<213> ORGANISM: Artificial
<220> FEATURE:
<223> OTHER INFORMATION: Secretion peptide

<400> SEQUENCE: 6
```

```
Met Arg Leu Leu Leu Leu Leu Leu Leu Pro Leu Ala Ala Leu Gly
1               5                   10                  15
```

<210> SEQ ID NO 7
<211> LENGTH: 19
<212> TYPE: PRT
<213> ORGANISM: Artificial
<220> FEATURE:
<223> OTHER INFORMATION: Secretion peptide

<400> SEQUENCE: 7

```
Met Leu Leu Gln Ala Phe Leu Phe Leu Leu Ala Gly Phe Ala Ala Lys
1               5                   10                  15

Ile Ser Ala
```

<210> SEQ ID NO 8
<211> LENGTH: 35
<212> TYPE: PRT
<213> ORGANISM: Artificial
<220> FEATURE:
<223> OTHER INFORMATION: Secretion peptide

<400> SEQUENCE: 8

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Glu Gly Val Ser Leu
            20                  25                  30

Glu Lys Arg
        35
```

<210> SEQ ID NO 9
<211> LENGTH: 22
<212> TYPE: PRT
<213> ORGANISM: Artificial
<220> FEATURE:
<223> OTHER INFORMATION: Secretion peptide

<400> SEQUENCE: 9

```
Met Arg Phe Pro Ser Ile Phe Thr Ala Val Leu Phe Ala Ala Ser Ser
1               5                   10                  15

Ala Leu Ala Ala Pro Val
            20
```

<210> SEQ ID NO 10
<211> LENGTH: 27
<212> TYPE: PRT
<213> ORGANISM: Artificial
<220> FEATURE:
<223> OTHER INFORMATION: Secretion peptide

<400> SEQUENCE: 10

```
Met Arg Phe Pro Ser Ile Phe Thr Ala Val Leu Phe Ala Ala Ser Ser
1               5                   10                  15

Ala Leu Ala Ala Pro Val Ser Leu Glu Lys Arg
            20                  25
```

<210> SEQ ID NO 11
<211> LENGTH: 41
<212> TYPE: PRT
<213> ORGANISM: Artificial
<220> FEATURE:
<223> OTHER INFORMATION: Secretion peptide

<400> SEQUENCE: 11

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Glu Gly Val Ser Leu
            20                  25                  30

Glu Lys Arg Glu Ala Glu Ala Glu Ala
            35                  40

<210> SEQ ID NO 12
<211> LENGTH: 85
<212> TYPE: PRT
<213> ORGANISM: Artificial
<220> FEATURE:
<223> OTHER INFORMATION: Secretion peptide

<400> SEQUENCE: 12

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg
            85

<210> SEQ ID NO 13
<211> LENGTH: 44
<212> TYPE: PRT
<213> ORGANISM: Artificial
<220> FEATURE:
<223> OTHER INFORMATION: Secretion peptide

<400> SEQUENCE: 13

Met Thr Lys Pro Thr Gln Val Leu Val Arg Ser Val Ser Ile Leu Phe
1               5                   10                  15

Phe Ile Thr Leu Leu His Leu Val Val Ala Leu Asn Asp Val Ala Gly
            20                  25                  30

Pro Ala Glu Thr Ala Pro Val Ser Leu Leu Pro Arg
            35                  40

<210> SEQ ID NO 14
<211> LENGTH: 22
<212> TYPE: PRT
<213> ORGANISM: Artificial
<220> FEATURE:
<223> OTHER INFORMATION: Secretion peptide

<400> SEQUENCE: 14

Met Phe Ser Pro Ile Leu Ser Leu Glu Ile Ile Leu Ala Leu Ala Thr
1               5                   10                  15

Leu Gln Ser Val Phe Ala
            20

<210> SEQ ID NO 15
<211> LENGTH: 22
<212> TYPE: PRT
<213> ORGANISM: Artificial
<220> FEATURE:
<223> OTHER INFORMATION: Secretion peptide -continued

```
<400> SEQUENCE: 15

Met Gln Thr Leu Leu Val Ser Ser Leu Val Val Ser Leu Ala Ala Ala
1               5                   10                  15

Leu Pro His Tyr Ile Arg
            20

<210> SEQ ID NO 16
<211> LENGTH: 22
<212> TYPE: PRT
<213> ORGANISM: Artificial
<220> FEATURE:
<223> OTHER INFORMATION: Secretion peptide

<400> SEQUENCE: 16

Met Ile Phe Leu Lys Leu Ile Lys Ser Ile Val Ile Gly Leu Gly Leu
1               5                   10                  15

Val Ser Ala Ile Gln Ala
            20

<210> SEQ ID NO 17
<211> LENGTH: 24
<212> TYPE: PRT
<213> ORGANISM: Artificial
<220> FEATURE:
<223> OTHER INFORMATION: Secretion peptide

<400> SEQUENCE: 17

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 18
<211> LENGTH: 18
<212> TYPE: PRT
<213> ORGANISM: Artificial
<220> FEATURE:
<223> OTHER INFORMATION: Secretion peptide

<400> SEQUENCE: 18

Met Lys Trp Val Thr Phe Ile Ser Leu Leu Phe Leu Phe Ser Ser Ala
1               5                   10                  15

Tyr Ser

<210> SEQ ID NO 19
<211> LENGTH: 24
<212> TYPE: PRT
<213> ORGANISM: Artificial
<220> FEATURE:
<223> OTHER INFORMATION: Secretion peptide

<400> SEQUENCE: 19

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 20
<211> LENGTH: 24
<212> TYPE: PRT
<213> ORGANISM: Artificial
<220> FEATURE:
<223> OTHER INFORMATION: Secretion peptide
```

```
<400> SEQUENCE: 20

Met Lys Tyr Thr Ser Tyr Ile Leu Ala Phe Gln Leu Cys Ile Val Leu
1               5                   10                  15

Gly Ser Leu Gly Cys Asp Leu Pro
            20

<210> SEQ ID NO 21
<211> LENGTH: 26
<212> TYPE: PRT
<213> ORGANISM: Artificial
<220> FEATURE:
<223> OTHER INFORMATION: Secretion peptide

<400> SEQUENCE: 21

Met Ala Ala Asp Ser Gln Thr Pro Trp Leu Leu Thr Phe Ser Leu Leu
1               5                   10                  15

Cys Leu Leu Trp Pro Gln Glu Pro Gly Ala
            20                  25

<210> SEQ ID NO 22
<211> LENGTH: 27
<212> TYPE: PRT
<213> ORGANISM: Artificial
<220> FEATURE:
<223> OTHER INFORMATION: Secretion peptide

<400> SEQUENCE: 22

Met Lys Lys Asn Arg Met Met Met Ile Trp Ser Val Gly Val Val
1               5                   10                  15

Trp Met Leu Leu Leu Val Gly Gly Ser Tyr Gly
            20                  25

<210> SEQ ID NO 23
<211> LENGTH: 18
<212> TYPE: PRT
<213> ORGANISM: Artificial
<220> FEATURE:
<223> OTHER INFORMATION: Secretion peptide

<400> SEQUENCE: 23

Met Gln Lys Leu Ile Ile Phe Ala Leu Val Val Leu Cys Val Gly Ser
1               5                   10                  15

Glu Ala

<210> SEQ ID NO 24
<211> LENGTH: 18
<212> TYPE: PRT
<213> ORGANISM: Artificial
<220> FEATURE:
<223> OTHER INFORMATION: Secretion peptide

<400> SEQUENCE: 24

Met Lys Ala Leu Ile Val Leu Gly Leu Val Leu Leu Ser Val Thr Val
1               5                   10                  15

Gln Gly

<210> SEQ ID NO 25
<211> LENGTH: 20
<212> TYPE: PRT
<213> ORGANISM: Artificial
<220> FEATURE:
<223> OTHER INFORMATION: Secretion peptide
```

```
<400> SEQUENCE: 25

Met Val Asp Gly Val Met Ile Leu Pro Val Leu Ile Met Ile Ala Leu
1               5                   10                  15

Pro Ser Pro Ser
            20

<210> SEQ ID NO 26
<211> LENGTH: 19
<212> TYPE: PRT
<213> ORGANISM: Artificial
<220> FEATURE:
<223> OTHER INFORMATION: Secretion peptide

<400> SEQUENCE: 26

Met Gly Ala Ala Ala Lys Leu Ala Phe Ala Val Phe Leu Ile Ser Cys
1               5                   10                  15

Ser Ser Gly

<210> SEQ ID NO 27
<211> LENGTH: 31
<212> TYPE: PRT
<213> ORGANISM: Artificial
<220> FEATURE:
<223> OTHER INFORMATION: Secretion peptide

<400> SEQUENCE: 27

Met Leu Ser Leu Lys Pro Ser Trp Leu Thr Leu Ala Ala Leu Met Tyr
1               5                   10                  15

Ala Met Leu Leu Val Val Val Pro Phe Ala Lys Pro Arg Ala
            20                  25                  30

<210> SEQ ID NO 28
<211> LENGTH: 22
<212> TYPE: PRT
<213> ORGANISM: Artificial
<220> FEATURE:
<223> OTHER INFORMATION: Secretion peptide

<400> SEQUENCE: 28

Met Asp Met Arg Val Pro Ala Gln Leu Leu Gly Leu Leu Leu Leu Trp
1               5                   10                  15

Leu Pro Gly Ala Lys Cys
            20
```